United States Patent
Sheldon et al.

(10) Patent No.: US 6,475,243 B1
(45) Date of Patent: Nov. 5, 2002

(54) ACETABULAR CUP ASSEMBLY WITH SELECTED BEARING

(75) Inventors: Michael B. Sheldon, Pymble (AU); Nicholas N. G. Dong, Little Falls, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/665,025

(22) Filed: Sep. 19, 2000

Related U.S. Application Data

(63) Continuation-in-part of application No. 09/083,406, filed on May 22, 1998.

(51) Int. Cl.$^7$ .................................................. A61F 2/32
(52) U.S. Cl. ................................. 623/22.28; 623/22.21
(58) Field of Search ........................... 623/22.21, 22.24, 623/22.25, 22.28, 22.26, 22.23, 22.17, 22.11, 22.12, 22.13, 22.14, 22.15, 22.19

(56) References Cited

U.S. PATENT DOCUMENTS

| | | | |
|---|---|---|---|
| D249,957 S | 10/1978 | Eicher et al. | |
| 4,666,448 A | 5/1987 | Ganz | |
| 4,695,282 A | 9/1987 | Forte et al. | |
| 4,715,860 A | 12/1987 | Amstutz et al. | |
| 4,822,369 A | * 4/1989 | Oueveau et al. | 623/22 |
| 4,921,500 A | 5/1990 | Averill et al. | |
| 4,969,910 A | 11/1990 | Noiles | |
| 5,080,678 A | 1/1992 | Spotorno et al. | |
| 5,092,898 A | 3/1992 | Bekki et al. | |
| 5,108,447 A | 4/1992 | Zeller et al. | |
| 5,156,626 A | 10/1992 | Broderick et al. | |
| 5,263,988 A | 11/1993 | Huebner | |
| 5,314,479 A | 5/1994 | Rockwood, Jr. et al. | |
| 5,326,368 A | 7/1994 | Collazo | |
| 5,376,122 A | 12/1994 | Pappas et al. | |
| 5,425,778 A | 6/1995 | Zichner et al. | |
| 5,507,825 A | 4/1996 | Frei | |
| 5,571,201 A | 11/1996 | Averill et al. | |
| 5,658,345 A | 8/1997 | Willi | |
| 5,782,929 A | 7/1998 | Sederholm | |

FOREIGN PATENT DOCUMENTS

| | | |
|---|---|---|
| EP | 453694 | 10/1991 |
| EP | 554214 | 8/1993 |
| EP | 0773007 | 5/1997 |
| WO | WO9522944 | 8/1995 |

OTHER PUBLICATIONS

Transcend Articulation System, Ceramic on ceramic articulation. Wright Medical Technology, Inc., 1996.

Osteonics Secur–Fit HA Ceramic on Ceramic Bearing System, undated.

Contact SPH Cups System, non–cemented. Lima–Lto Medial Systems, undated.

* cited by examiner

*Primary Examiner*—Corrine McDermott
*Assistant Examiner*—Alvin Stewart
(74) *Attorney, Agent, or Firm*—Arthur Jacob

(57) ABSTRACT

An acetabular cup assembly allows pre-operative or inter-operative selection and securement of a bearing member within a shell member of the acetabular cup assembly, the bearing member being selected from a plurality of bearing members having different characteristics, including bearing characteristics, securement characteristics, position characteristics and orientation characteristics, so as to enable a surgeon to select those characteristics most appropriate to a particular patient, as determined by a pre-operative assessment or by an evaluation of conditions encountered at an implant site during the implant procedure, and to incorporate the desired characteristics into the acetabular cup assembly with ease and economy.

34 Claims, 13 Drawing Sheets

ACETABULAR CUP ASSEMBLY WITH SELECTED BEARING

This is a continuation-in-part of application Ser. No. 09/083,406, filed May 22, 1998, for ACETABULAR CUP ASSEMBLY WITH SELECTED BEARING.

The present invention relates generally to prosthetic implants and pertains, more specifically, to the implant of acetabular cup assemblies which secure a prosthetic bearing member in the acetabulum for the reception of a femoral head of a prosthetic hip joint.

The replacement of members of a natural hip joint with prosthetic implants has become widespread and is being accomplished with ever-increasing frequency. The variety of conditions encountered when effecting such implants has led to the use of various bearing materials placed at an optimum position and orientation, as determined by conditions encountered at the site of the implant. The choice of a particular material for the bearing, as well as the size, positioning and orientation of the bearing member, is determined by the surgeon performing the procedure. Usually such choices are made on the basis of a pre-operative assessment of the needs of a particular patient; however, at times the choices are not completed until the implant site actually is being prepared and conditions encountered at the site can be evaluated during the implant procedure itself. Accordingly, it would be advantageous to have available a greater range of interoperative choice, as well as pre-operative choice, so as to enable a surgeon to accommodate the needs of a particular patient as determined by either or both a pre-operative assessment and an evaluation of conditions encountered at a particular implant site, and to do so in a practical manner.

The present invention provides the surgeon with the ability to choose, either pre-operatively or interoperatively, an optimum material, position and orientation for a bearing member of an acetabular cup assembly to be implanted at a particular implant site, with increased ease and at lowered expense. As such, the present invention attains several objects and advantages, some of which are summarized as follows: Accommodates a wider choice of bearing materials in the bearing member of an acetabular cup assembly, while utilizing a common acetabular shell; enables the choice of size, position and orientation of the bearing surface of a bearing member selected for assembly with a particular acetabular shell; increases the range of bearing materials, as well as bearing size, positioning and orientation, and renders the choices available in a practical manner for either pre-operative or interoperative selection; allows a surgeon greater latitude in accommodating the needs of different patients while meeting the requirements imposed by various conditions encountered at a particular implant site, and enables appropriate choices to be made interoperatively, as well as pre-operatively; promotes greater accuracy in the replacement of a natural hip joint, with increased economy; provides a surgeon with the ability to make both pre-operative choices and interoperative choices from a wider range of options; enables the securement of a bearing member of selected material within a common acetabular shell, with increased ease and economy, and without complex, specialized instruments; facilitates the insertion and securement of a selected bearing member within an acetabular shell in appropriate alignment and orientation of the bearing member within the acetabular shell; provides an acetabular cup assembly having a bearing member of appropriate bearing material and accurate sizing, positioning and orientation, with economy of manufacture and use, and long-term reliability.

The above objects and advantages, as well as further objects and advantages, are attained by the present invention which may be described briefly as an acetabular cup assembly for receiving a proximal end of a femoral component of a prosthetic hip implant, the femoral component including a head member and a neck member depending from the head member, the acetabular cup assembly having an external shell member with an internal cavity, and an internal bearing member for securement within the cavity to receive the head member of the femoral component for rotational movement within the bearing member, the internal bearing member being selected from a plurality of bearing members having different characteristics such that the acetabular cup assembly selectively is provided with characteristics corresponding to the characteristics of the selected internal bearing member, the acetabular cup assembly comprising: a metallic securing member for reception within the cavity of the acetabular shell, the securing member extending between and upper end and a lower end and including an external securing element and an internal receptor element; an external receptor element on the bearing member, the external receptor element and the internal receptor element being compatible with particular characteristics of the bearing member such that upon engagement of the external receptor element with the internal receptor element the internal bearing member is secured to the securing member with the lower end of the bearing member spaced upwardly a prescribed distance from the lower end of the securing member; and an internal securing element within the cavity of the shell member, the internal securing element being essentially complementary to the external securing element of the securing member such that upon selective engagement of the external securing element with the internal securing element the securing member is secured selectively within the shell member; the prescribed distance between the lower end of the bearing member and the lower end of the securing member being such that contact between the neck member of the femoral component and the lower end of the securing member precludes deleterious impingement of the femoral component upon the bearing member.

Further, the present invention provides a shell member for use in an acetabular cup assembly having an internal bearing member for securement within the shell member, the internal bearing member being selected from a plurality of bearing members having different characteristics such that the acetabular cup assembly selectively is provided with characteristics corresponding to the characteristics of the selected internal bearing member, the shell member comprising: an internal cavity; a first securing element within the cavity of the shell member, the first securing element being compatible with the securing characteristics of at least one of the plurality of internal bearing members; and a second securing element within the cavity of the shell member, the second securing element being compatible with the securing characteristics of at least another of the plurality of internal bearing members; the first and second securing elements being juxtaposed with one another and placed at relative locations such that the effectiveness of each of the first and second securing elements is maintained in the presence of the other of the first and second securing elements, whereby the one and the another of the internal bearing members each is selectable for effective securement within the shell member to complete the acetabular cup assembly.

In addition, the present invention includes a kit of component parts for assembling an acetabular cup assembly having an internal bearing member secured within a shell member, the kit comprising: a plurality of bearing members having different characteristics such that the acetabular cup assembly selectively is provided with characteristics corresponding to the characteristics of a selected one of the internal bearing members; the shell member comprising: an internal cavity; a first securing element within the cavity of the shell member, the first securing element being compatible with the securing characteristics of at least one of the plurality of internal bearing members; and a second securing element within the cavity of the shell member, the second securing element being compatible with the securing characteristics of at least another of the plurality of internal bearing members; the first and second securing elements being juxtaposed with one another and placed at relative locations such that the effectiveness of each of the first and second securing elements is maintained in the presence of the other of the first and second securing elements, whereby the one and the another of the internal bearing members each is selectable for effective securement within the shell member as the selected one bearing member to complete the acetabular cup assembly.

Still further, the present invention provides an improvement in a method for implanting an acetabular cup assembly having an external shell member with an internal cavity, and an internal bearing member for securement within the cavity, the internal bearing member being selected from a plurality of bearing members having different characteristics such that the acetabular cup assembly selectively is provided with characteristics corresponding to the characteristics of the selected internal bearing member, the improvement comprising the steps of: providing a first securing element within the cavity of the shell member, the first securing element being compatible with the securing characteristics of at least one of the plurality of internal bearing members; providing a second securing element within the cavity of the shell member, the second securing element being compatible with the securing characteristics of at least another of the plurality of internal bearing members; and selecting the one or the another of the internal bearing members and securing the selected internal bearing member within the shell member by engaging the selected internal bearing member with the corresponding first securing element or second securing element for completion of the acetabular cup assembly.

The invention will be understood more fully, while still further objects and advantages will become apparent, in the following detailed description of preferred embodiments of the invention illustrated in the accompanying drawing, in which.

Figure 1:
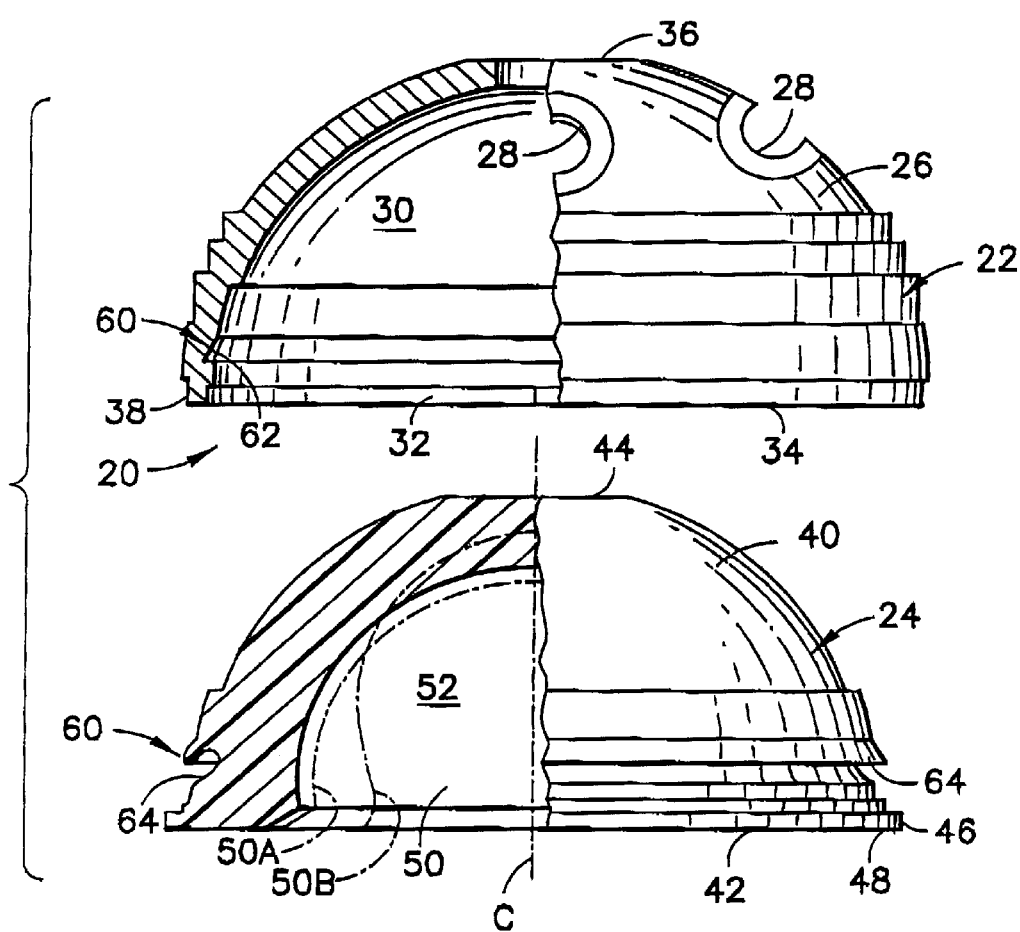
FIG. 1 is an exploded elevational view, partially sectioned, of an acetabular cup assembly constructed in accordance with the present invention.
Figure 2:
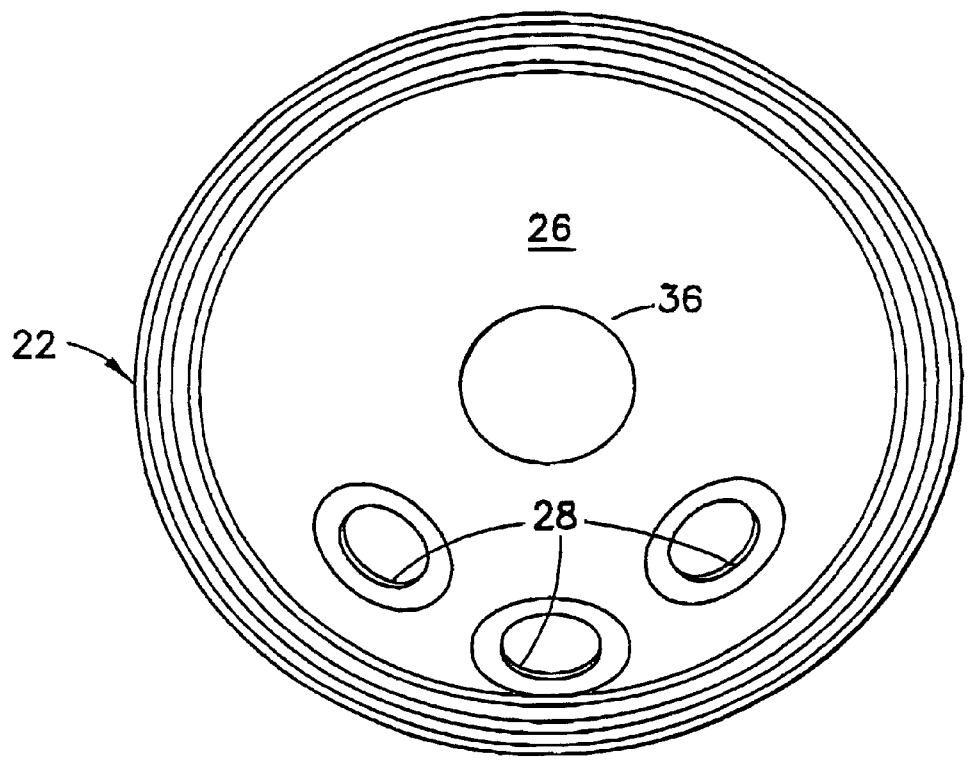
FIG. 2 is a top plan view of the shell component of the acetabular cup assembly.
Figure 3:
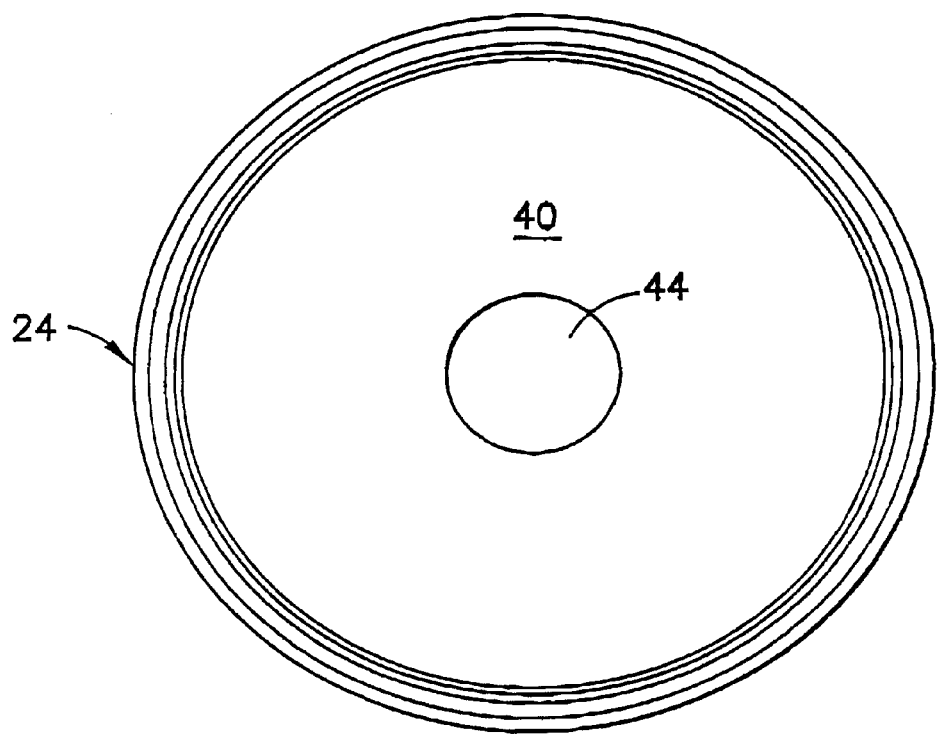
FIG. 3 is a top plan view of the bearing insert component of the acetabular cup assembly.

Referring now to the drawing, and especially to FIGS. 1 through 3 thereof, an acetabular cup assembly constructed in accordance with the present invention is illustrated generally at 20. Acetabular cup assembly 20 includes a shell component in the form of metallic shell member 22 and a bearing insert which, in this instance, is in the form of a plastic bearing member 24. Shell member 22 includes an outer surface 26 having a profile configuration which enables the shell member 22 to be seated and fixed in place within an appropriately prepared acetabulum in a now well-known manner. A plurality of screw holes 28 are provided in the shell member 22 for receiving anchoring screws (not shown) when such supplemental securing means are desired. An inner cavity 30 extends upwardly into shell member 22, from a lower opening 32 at a lower end 34 toward an upper end 36. A rim 38 is located at the lower end 34.

Bearing member 24 has a generally domed exterior 40 which is essentially complementary to the cavity 30 of the shell member 22 and extends longitudinally from a base 42 to a top 44. A basal flange 46 extends circumferentially around the base 42 of the bearing member 24 and projects laterally outwardly to provide a transverse bearing face 48 at the base 42 of the bearing member 24. A bearing socket 50 extends upwardly into the bearing member 24 and provides a spherical bearing surface 52 for a complementary femoral head (not shown).

Acetabular cup assembly 20 is to be implanted in stages; that is, the shell member 22 and the bearing member 24 are to be assembled interoperatively, so as to enable appropriate sizing, placement and orientation of the bearing socket 50, based upon a pre-operative assessment or upon an evaluation of conditions encountered at the site of the implant. To that end, alternate bearing members 24 are made available, in a kit of component parts, which kit provides a plurality of bearing members, the alternate bearing members 24 providing corresponding bearing sockets 50 placed at different locations and orientations, relative to the seated and secured shell member 22, any one of which bearing sockets 50 then being capable of securement in place in the shell member 22, interoperatively, with the bearing surface 52 appropriately located and oriented for accommodating the needs of the patient.

Figure 4:
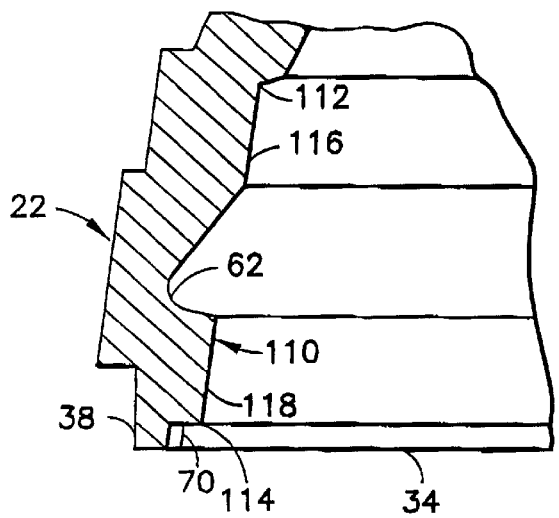
FIG. 4 is an enlarged fragmentary view of a portion of the shell component as illustrated in FIG. 1.
Figure 6:
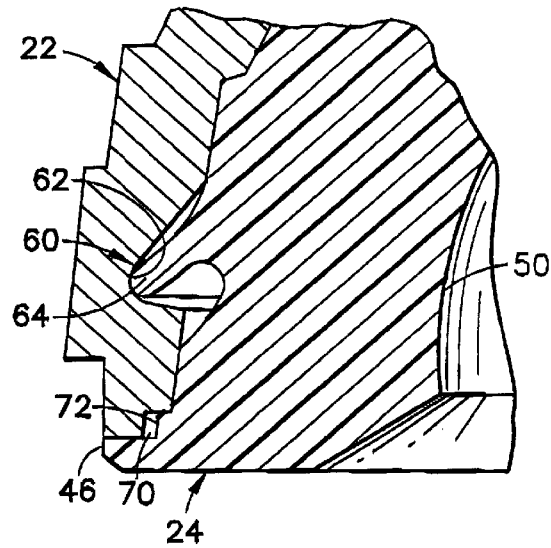
FIG. 6 is an enlarged fragmentary view of the portions shown in FIGS. 4 and 5, with the acetabular cup assembly assembled.
Figure 5:
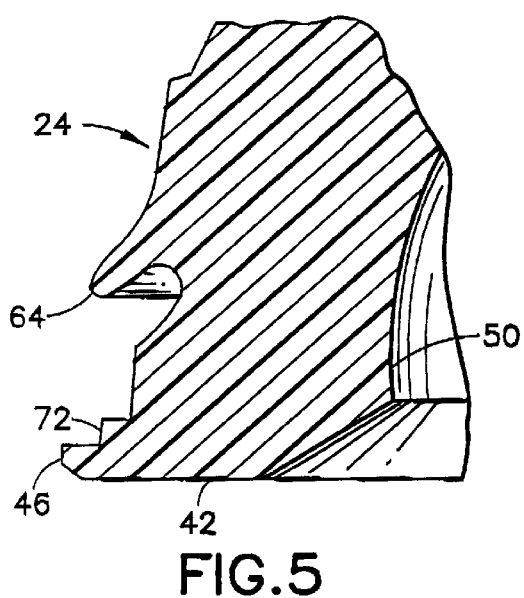
FIG. 5 is an enlarged fragmentary view of a portion of the bearing insert component as illustrated in FIG. 1.
Figure 7:
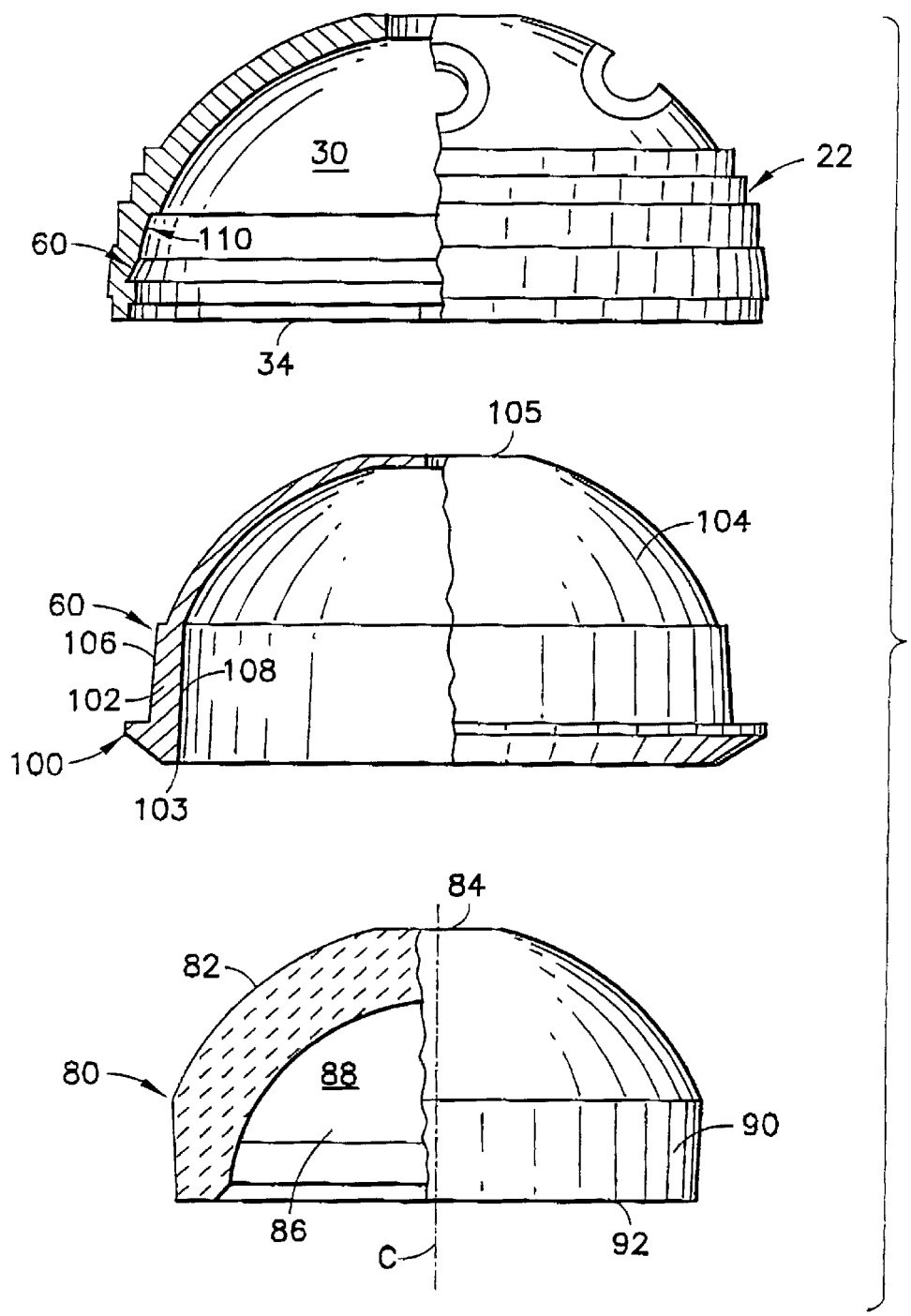
FIG. 7 is an exploded elevational view, partially sectioned, of the acetabular cup assembly shown utilizing alternate component parts.
Figure 8:
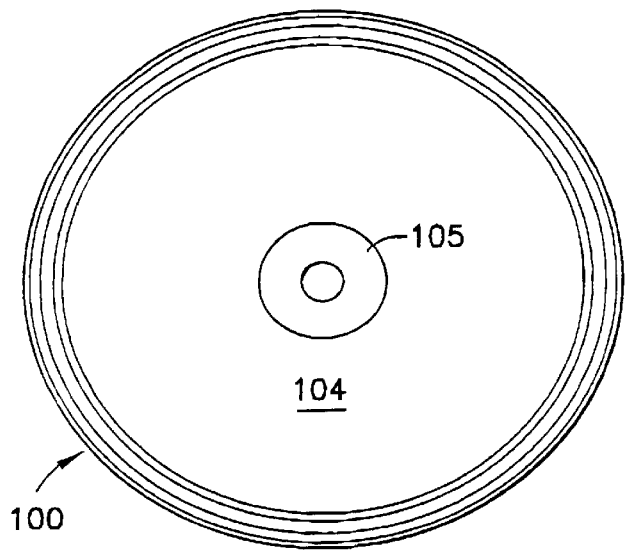
FIG. 8 is a top plan view of a securing component of the acetabular cup assembly.
Figure 9:
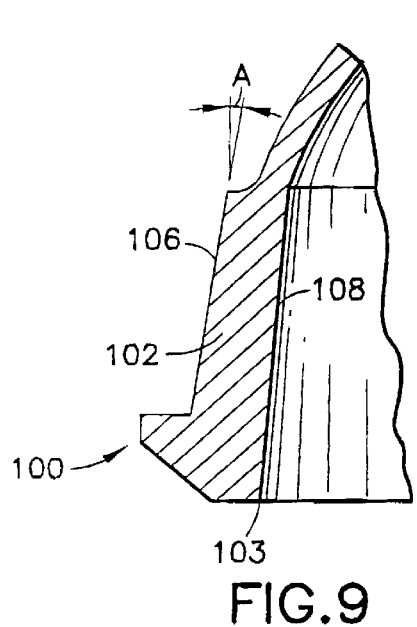
FIG. 9 is an enlarged fragmentary view of a portion of the securing component as illustrated in FIG. 7.

A selected bearing member 24 is secured in place appropriately within the shell member 22 by means of a securing mechanism 60 provided adjacent the lower end 34 of the shell member 22 and adjacent the base 42 of the bearing member 24. Turning now to FIGS. 4 through 6, as well as to FIGS. 1 through 3, securing mechanism 60 is seen to include a securing element in the form of an annular recess 62 extending laterally outwardly into the shell member 22 adjacent the lower end 34. a complementary securing element in the form of an annular rib 64 extends laterally outwardly from the bearing member 24, adjacent the base 42 of the bearing member 24. A preferred material for the plastic bearing member 24 is an ultra-high molecular weight polyethylene commonly used in connection with such bearing members, the securing characteristics of which material include a resiliency sufficient to assure that upon inserting the bearing member 24 into the shell member 22, and seating the bearing member 24 in the shell member 22, as seen in FIG. 6, the annular rib 64 is seated within the annular recess 62 to secure the bearing member 24 within the shell member 22.

The position and orientation of the bearing socket 50 relative to the fixed shell member 22 are selected by providing the different locations and orientations of the bearing socket 50 within the bearing member 24, as set forth above. Thus, as seen in FIG. 1, the bearing socket 50 may be offset from the central axis C of the bearing member 24, as illustrated in phantom by an alternate offset bearing socket 50A, by varied amounts in different selectable bearing members 24, for the selection of an appropriate position for the bearing socket 50 at the implant site. Likewise, an appropriate orientation of bearing socket 50 is made available through the provision of alternate angled orientations, as illustrated in phantom by an alternately oriented bearing socket 50B in FIG. 1. Once seated in place, the selected bearing member 24 is secured within the shell member 22 by engagement of the complementary securing elements in the form of recess 62 and rib 64, common to the securing mechanism 60 provided for all of the alternate bearing members 24. In addition, once the selected bearing member 24 is seated appropriately within the shell member 22, rotation of the bearing member 24 about the axis C relative to the shell member 22 is precluded by engagement of protrusions 70 extending radially inwardly from the rim 38 of the shell member 22 with counterpart portions 72 of the bearing member 24, adjacent the flange 46 of the bearing member 24.

Should the surgeon determine, either on the basis of a pre-operative assessment of a patient or during the course of the implant procedure, that based upon the needs of a particular patient, as determined by the pre-operative assessment or by an evaluation of conditions encountered at the particular implant site, a bearing material having characteristics other than those of the material of bearing member 24 would be more appropriate, acetabular cup assembly 20 provides the surgeon with the ability to choose a bearing member having a bearing material which exhibits characteristics more appropriate to the needs of that particular patient. Thus, as seen in FIGS. 7 through 10, an alternate bearing member 80, provided as another of the plurality of bearing members made available in the aforesaid kit, is constructed of a ceramic material and includes a generally domed exterior portion 82 which extends to a top 84. A bearing socket 86 extends upwardly into the bearing member 80 and provides a spherical bearing surface 88 for a complementary femoral head (not shown).

One of the most effective, convenient, mechanically simple and easily used securement mechanisms available for securing together mechanical components, where neither component is constructed of a resilient material such as the material of plastic bearing member 24, is mating tapered surfaces. The degree to which the tapered surfaces are tapered depends upon securing characteristics of the particular materials being secured together. However, the securing characteristics of ceramic bearing member 80 are such that securement of the bearing member 80 is best accomplished with a securement surface which is essentially cylindrical. Accordingly, bearing member 80 is provided with an external receptor element in the form of a generally cylindrical securement surface 90 which extends essentially parallel to the central axis C of the bearing member 80, between lower end 92 of the bearing member 80 and the domed exterior portion 82. In order to enable simplified interoperative securement of the bearing member 80 within shell member 22, subsequent to locating and seating shell member 22 within the acetabulum, securing mechanism 60 provides appropriate mating tapered surfaces. Thus, securing mechanism 60 includes a metallic securing member shown in the form of a sleeve 100 having an annular ring portion 102 adjacent a lower end 103 and a domed portion 104 extending between the ring portion 102 and an upper end 105. The domed portion 104 is essentially complementary to the counterpart portion of the inner cavity 30 of the shell member 22, and the ring portion 102 is provided with an external securing element in the form of an external seating surface 106 and an internal receptor element in the form of a generally cylindrical internal securement surface 108. The configuration of the internal securement surface 108 and the configuration of the external securement surface 90 are compatible with the particular characteristics of the material of the bearing member 80 so that upon engagement of the external securement surface 90 with the internal securement surface 108, as by an interference fit, the bearing member 80 is secured to the sleeve 100.

Figure 10:
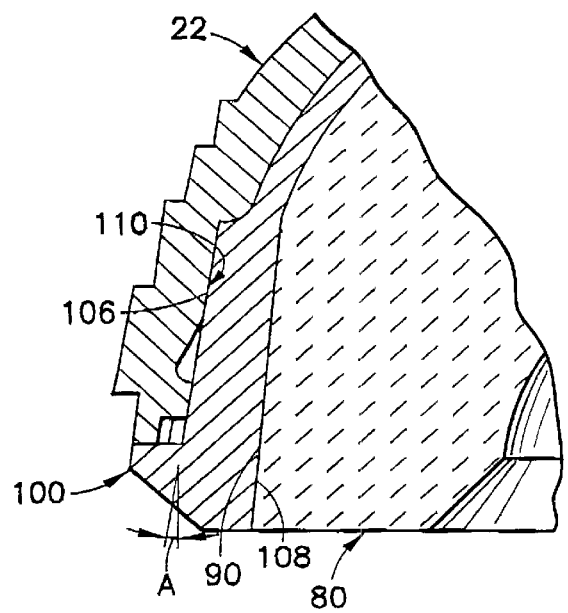
FIG. 10 is an enlarged fragmentary cross-sectional view of a portion of the acetabular cup assembly illustrated in FIG. 7, with the component parts assembled.

Securing mechanism 60 further includes an internal securing element in the form of internal seating surface 110 located on the shell member 22, within the cavity 30 adjacent the lower end 34 of the shell member 22. Internal seating surface 110 is generally complementary to external seating surface 106 for mating engagement of the seating surfaces 106 and 110, as seen in FIG. 10. The seating surfaces 106 and 110 are provided with a tapered configuration, as illustrated by angle A, the taper of the configuration being compatible with the securing characteristics of the material of the sleeve 100 and the shell member 22 such that the sleeve 100 is secured within the shell member 22 by virtue of the locking of the tapered seating surfaces 106 and 110 in response to engagement of the seating surfaces 106 and 110. In the preferred embodiment, the shell member 22 and the sleeve 100 are constructed of commercially pure titanium and the angle A is about 6°. Seating surface 110 includes an upper end 112 and a lower end 114 and is divided by the recess 62 into an upper segment 116 and a lower segment 118 (see FIG. 4). By placing the recess 62 essentially midway between the upper end 112 and the lower end 114, engagement of the seating surfaces 106 and 110, and the locking of the seating surfaces 106 and 110 in response to such engagement, is facilitated by virtue of the locking being accomplished along segments 116 and 118 having generally the same, and therefore maximized, axial length. In this manner, the effectiveness of the seating surface 110 in assuring appropriate alignment between the sleeve 100 and the shell member 22 as the sleeve 100 is inserted into the shell member 22 and in subsequently attaining the desired locking engagement with seating surface 106 is not compromised by the presence of the recess 62.

Figure 11:
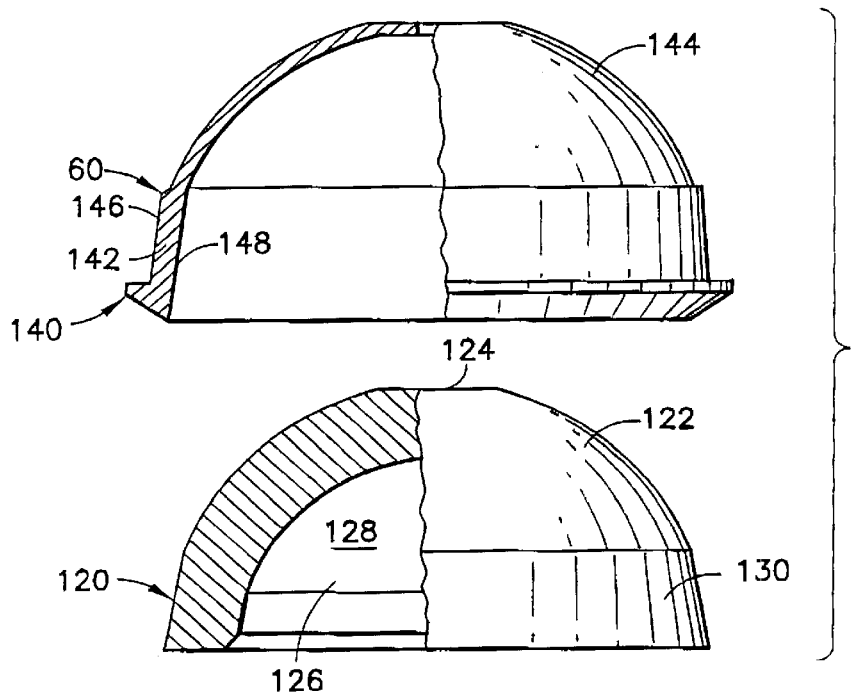
FIG. 11 is an exploded elevational view, partially sectioned, of an alternate securing component and bearing insert component for the acetabular cup assembly.
Figure 12:
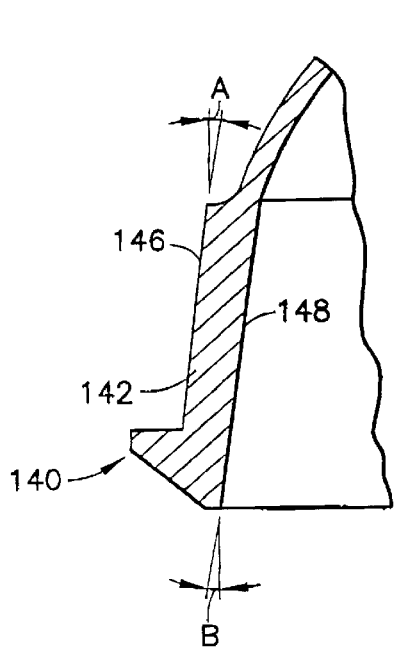
FIG. 12 is an enlarged fragmentary view of a portion of the securing component of FIG. 11.
Figure 13:
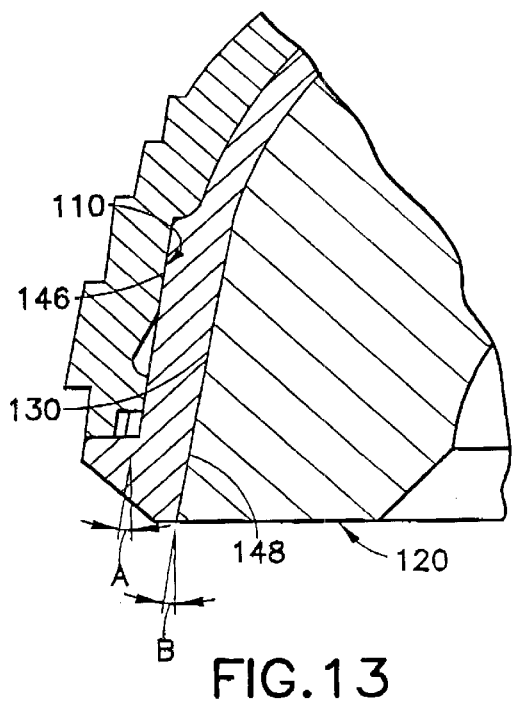
FIG. 13 is an enlarged fragmentary view of portions of the acetabular cup assembly utilizing the alternate component parts illustrated in FIG. 11, with the component parts assembled.

Referring now to FIGS. 11 through 13, should the surgeon desire to employ another material as a bearing material in the acetabular cup assembly 20, another alternative bearing member constructed of that material is available in the aforesaid kit of component parts for securement within the shell member 22. Thus, alternate bearing member 120 is constructed of another metal, such as, for example, a cobalt-chrome alloy. Bearing member 120 includes a generally domed exterior portion 122 which extends to a top 124. A bearing socket 126 extends upwardly into the bearing member 120 and provides a spherical bearing surface 128 for a complementary femoral head (not shown). Bearing member 120 is provided with an external receptor element in the form of an external securing surface 130. Here again, securing mechanism 60 includes a metallic securing member shown in the form of a sleeve 140 having an annular ring portion 142 and a domed portion 144. The domed portion 144 is essentially complementary to the counterpart portion of the inner cavity 30 of the shell member 22, and the ring portion 142 is provided with an external securing element in the form of an external seating surface 146 and an internal receptor element in the form of an internal securement surface 148.

The configuration of the internal securement surface 148 and the configuration of the external securement surface 130 are compatible with the particular securing characteristics of the material of the bearing member 120 so that upon engagement of the external securement surface 130 with the internal securement surface 148, the bearing member 120 is secured to the sleeve 140 in response to such engagement and seating of the sleeve 140 on the bearing member 120. To that end, the securement surfaces 130 and 148 are tapered at an angle B which effects a secure lock between the bearing member 120 and the sleeve 140. The sleeve 140, in turn, is secured within the shell member 22 by the lock effected between the seating surfaces 146 and 110. In the preferred embodiment, sleeve 140 and shell member 22 both are constructed of commercially pure titanium and the seating surfaces 146 and 110 are tapered at angle A, compatible with the securing characteristics of the material of sleeve 140 and shell member 22, as described above in connection with sleeve 100. In this manner, the shell member 22 is able to receive any selected one of a plurality of bearing members constructed of different materials, such as bearing members 24, 80 and 120, furnished in the aforesaid kit, with securement of the selected bearing member being effected either pre-operatively or interoperatively with ease, accuracy and minimal effort on the part of the surgeon, and without the necessity for complex special instruments.

Figure 14:
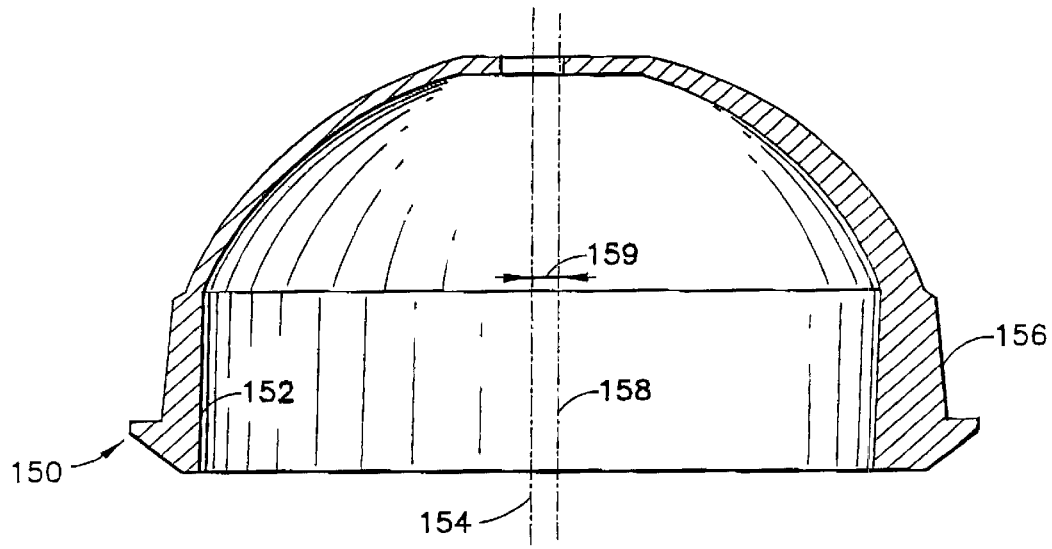
FIG. 14 is an elevational cross-sectional view of an alternate securing component.

Turning now to FIG. 14, where it is desired to select a particular position of the bearing surface of a bearing member relative to a shell member within which the bearing member is to be secured, utilizing a metallic securing member in the form of a sleeve constructed in accordance with the present invention, alternate sleeves are provided in which the relative location of the internal receptor element and the external securing element of the sleeve differ from sleeve to sleeve. Thus, in an alternate sleeve 150, the internal receptor element includes an internal securement surface 152 having a central axis 154 which extends in a longitudinal direction, the external securing element includes an external seating surface 156 having a central axis 158 which extends in a longitudinal direction, and the central axis 154 is offset laterally from the central axis 158, as seen at 159. A desired position of the bearing surface of a bearing member is attained by selecting a sleeve 150 having a particular offset 159.

Figure 15:
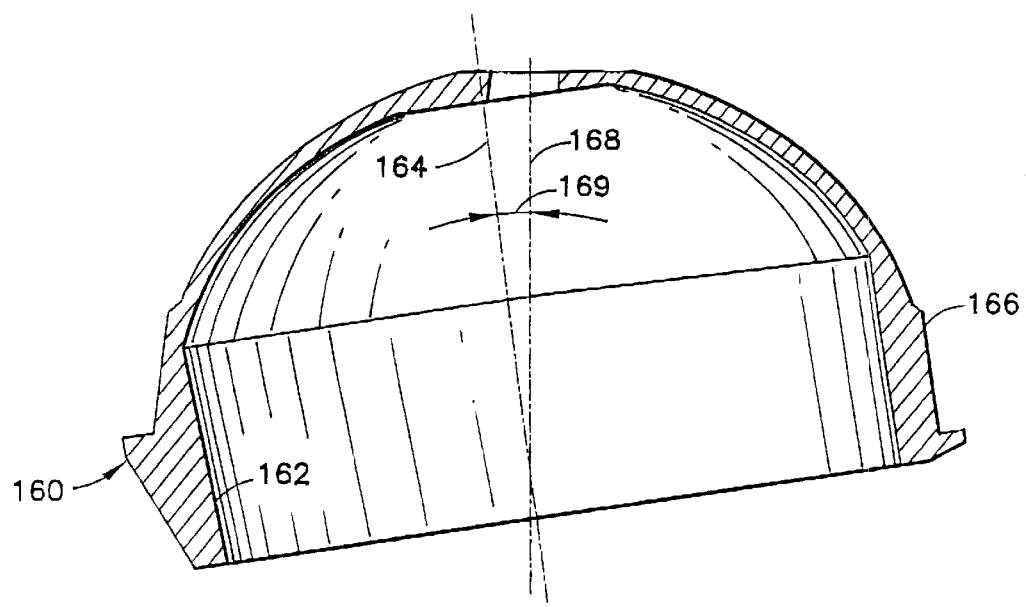
FIG. 15 is an elevational cross-sectional view of another alternate securing component.

A desired orientation of the bearing surface of a bearing member is attained by selecting a sleeve which provides that orientation. As seen in FIG. 15, an alternate sleeve 160 includes an internal securement surface 162 having a central axis 164 which extends in a longitudinal direction, the external securing element includes an external seating surface 166 having a central axis 168 which extends in a longitudinal direction, and the central axis 164 makes an acute angle 169 with the central axis 168 such that the selection of the magnitude of angle 169 results in a concomitant selection of the relative orientation of the surfaces 162 and 166. A desired orientation of the bearing surface of a bearing member is attained by selecting a sleeve 160 having a particular angle 169.

It will be understood that the selected positioning and the selected orientation described in connection with sleeves 150 and 160 are illustrative examples only. Various combinations of positioning and orientation, as well as other positions and orientations, are available by modifying the configuration of the metallic securing member to accommodate the desired positioning and orientation of the bearing surface of a particular bearing member.

Figure 16:
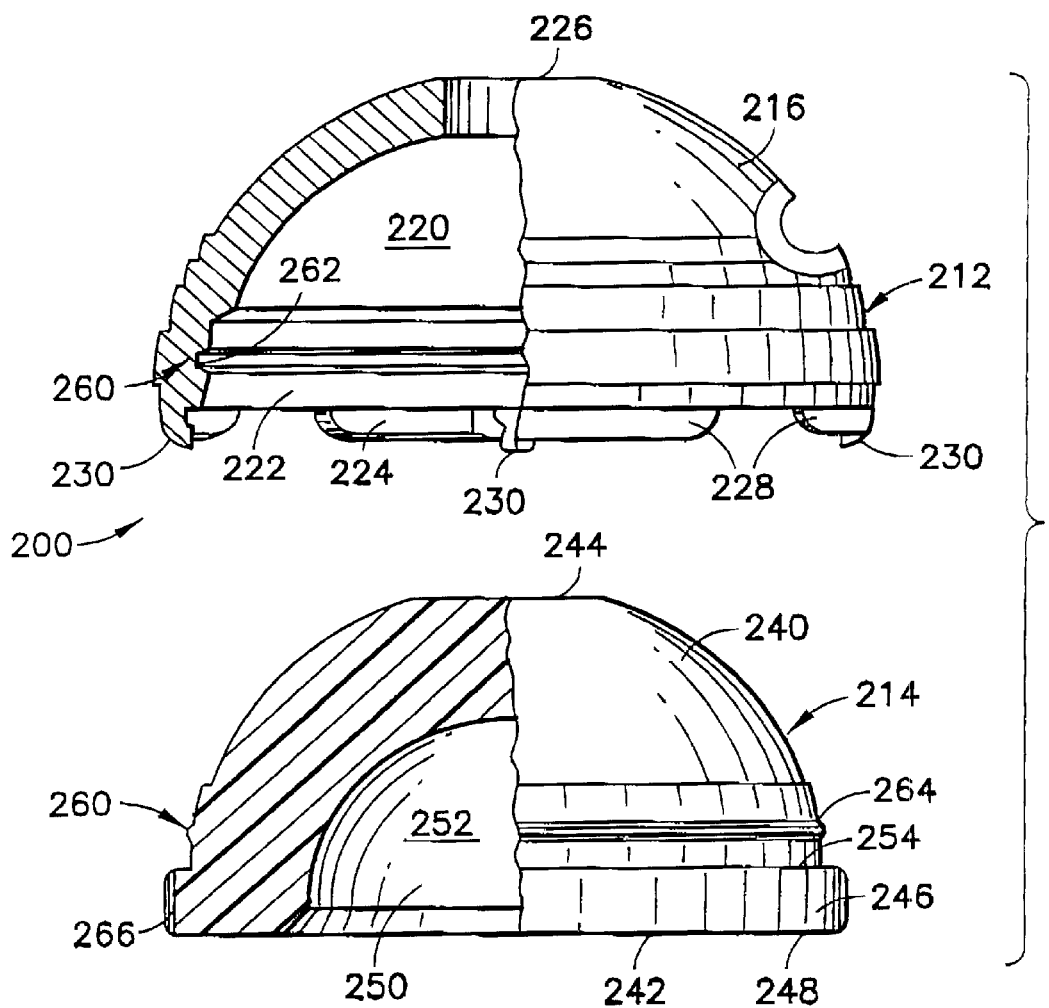
FIG. 16 is an exploded elevational view, partially sectioned, of another acetabular cup assembly constructed in accordance with the present invention.
Figure 17:
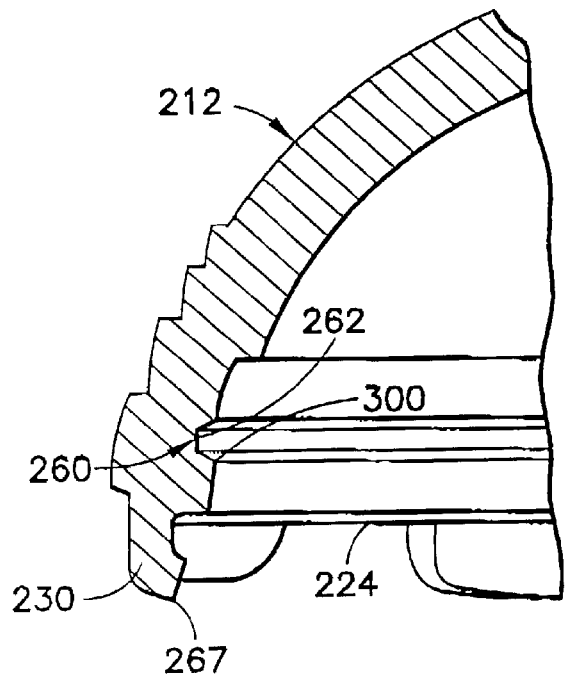
FIG. 17 is an enlarged fragmentary view of a portion of the shell component illustrated in FIG. 16.
Figure 18:
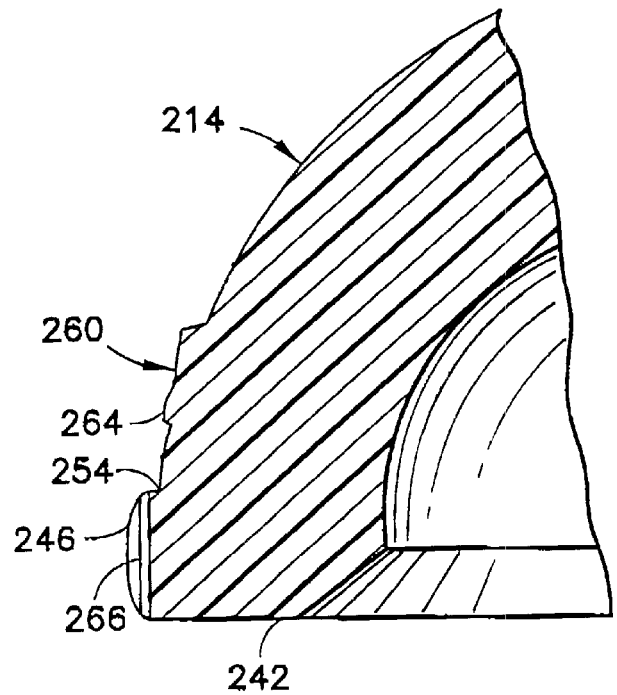
FIG. 18 is an enlarged fragmentary view of a portion of the bearing insert component illustrated in FIG. 16.

Referring now to FIGS. 16 through 18, another embodiment of the invention is illustrated in the form of acetabular cup assembly 200. Acetabular cup assembly 200 includes a shell component in the form of metallic shell member 212 and a bearing insert which, in this instance, is in the form of a plastic bearing member 214. Shell member 212 has an outer surface 216 having a profile configuration which enables the shell member 212 to be seated and fixed in place within an appropriately prepared acetabulum in a now well-known manner. An inner cavity 220 extends upwardly into shell member 212, from a lower opening 222 at a lower end 224 toward an upper end 226. Rim segments 228 are located at the lower end 224, and fingers 230 depend from the rim segments 228, the preferred number of fingers 230 being four, spaced apart at ninety degrees from one another, for purposes to be set forth in detail below.

Bearing member 214 has a generally domed exterior 240 which is essentially complementary to the cavity 220 of the shell member 212 and extends longitudinally from a base 242 to a top 244. A basal flange 246 extends circumferentially around the base 242 of the bearing member 214 and projects laterally outwardly to provide a transverse bearing face 248 at the base 242 of the bearing member 214. A bearing socket 250 extends upwardly into the bearing member 214 and provides a spherical bearing surface 252 for a complementary femoral head (not shown). Basal flange 246 includes an upper lateral surface 254.

Acetabular cup assembly 200 is to be implanted in stages; that is, the shell member 212 and the bearing member 214 are to be assembled interoperatively, so as to enable appropriate sizing, placement and orientation of the bearing socket 250, based upon a pre-operative assessment or upon an evaluation of conditions encountered at the site of the implant. To that end, alternate bearing members 214 are made available, the alternate bearing members 214 providing corresponding bearing sockets 250 placed at different locations and orientations, relative to the seated and secured shell member 212, any one of which bearing sockets 250 then being capable of securement in place in the shell member 212, interoperatively, with the bearing surface 252 appropriately located and oriented for accommodating the needs of the patient. Thus, a kit of component parts which include a plurality of bearing members is made available for the selection of an appropriate bearing member 214.

Figure 19:
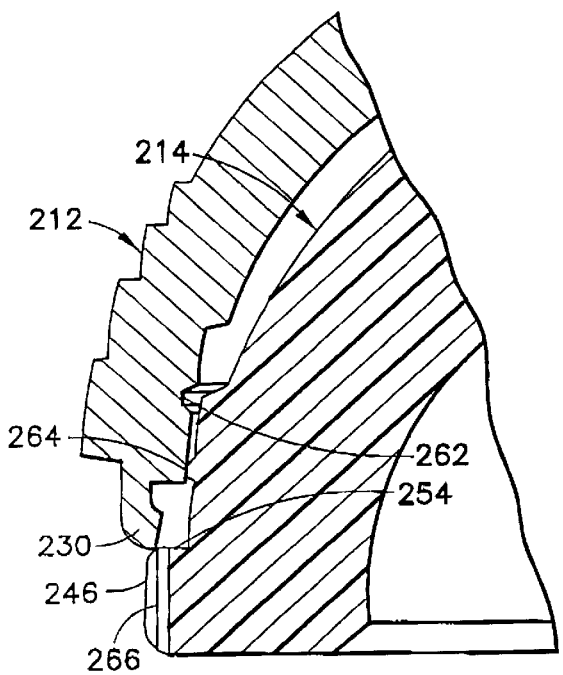
FIG. 19 is an enlarged fragmentary view of the portions shown in FIGS. 17 and 18, as the bearing insert component is being inserted into the shell component.
Figure 20:
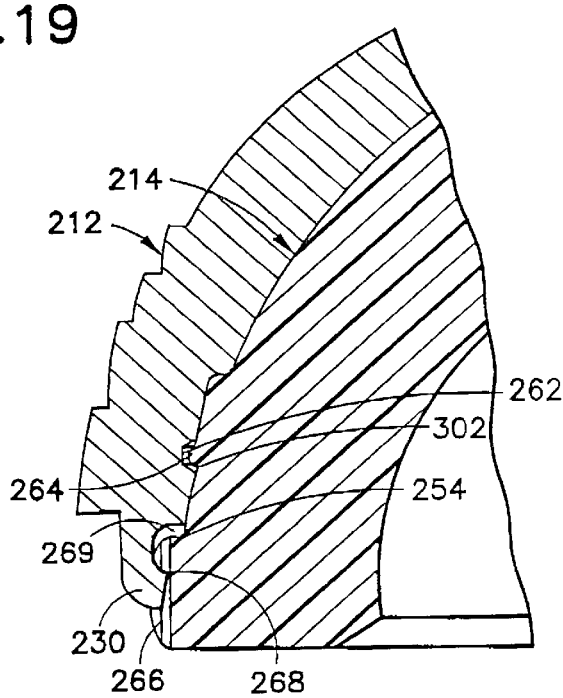
FIG. 20 is an enlarged fragmentary view of the portions shown in FIGS. 17 and 18, with the acetabular cup assembly assembled.
Figure 22:
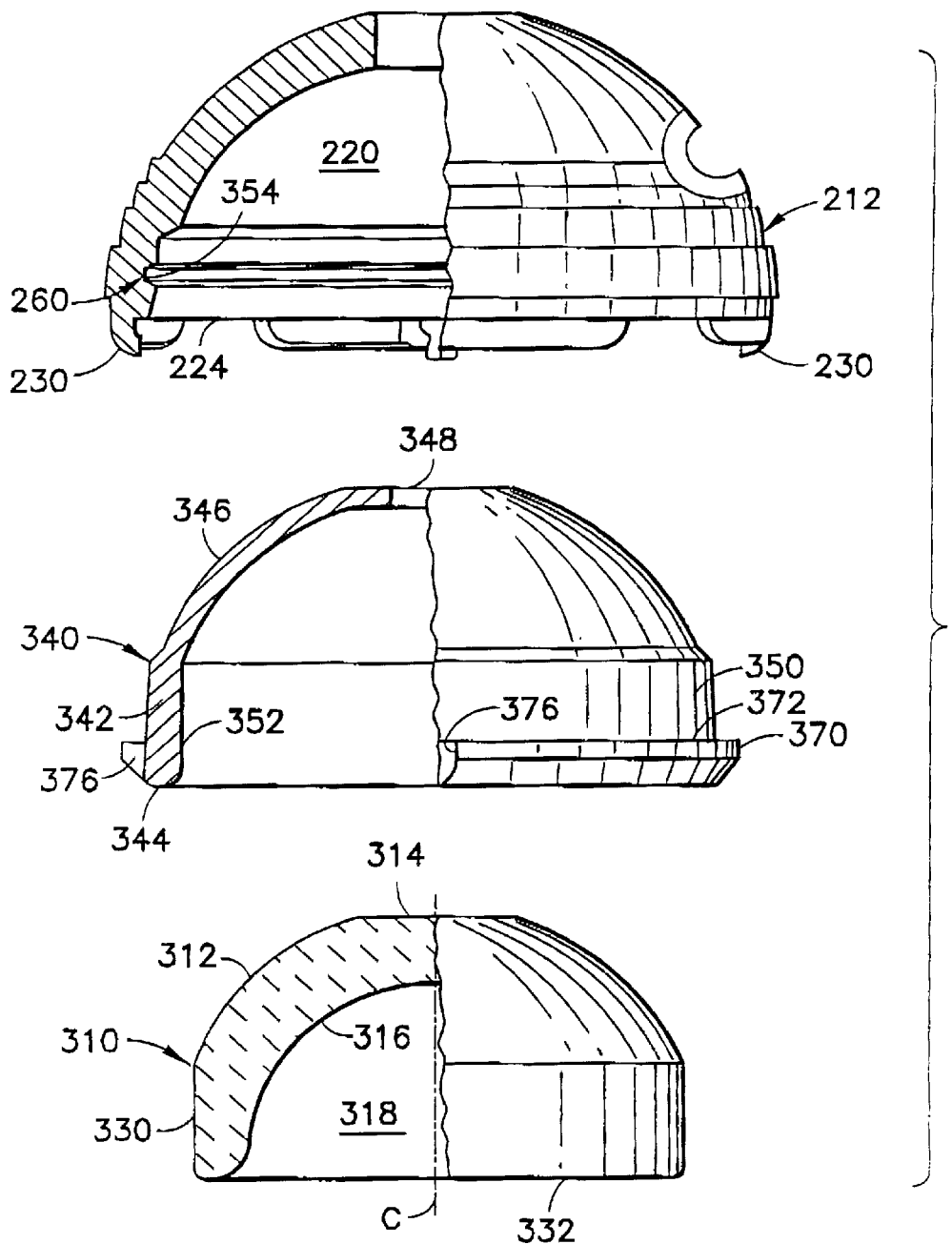
FIG. 22 is an exploded elevational view, partially sectioned, showing another embodiment including an assembly in which a bearing component is to be assembled with a securing component.

A selected bearing member 214 is secured in place appropriately within the shell member 212 by means of a securing mechanism 260 provided adjacent the lower end 224 of the shell member 212 and adjacent the base 242 of the bearing member 214. Turning now to FIGS. 19 and 20, as well as to FIGS. 16 through 18, securing mechanism 260 is seen to include a securing element in the form of an annular recess 262 extending laterally outwardly into the shell member 212 adjacent the lower end 234. a complementary securing element in the form of an annular rib 264 extends laterally outwardly from the bearing member 214, adjacent the base 242 of the bearing member 214. A preferred material for the plastic bearing member 214 is an ultra-high molecular weight polyethylene commonly used in connection with such bearing members, the securing characteristics of which material include a resiliency sufficient to assure that upon inserting the bearing member 214 into the shell member 212, and seating the bearing member 214 in the shell member 212, as seen in FIG. 20, the annular rib 264 is seated within the annular recess 262 to secure the bearing member 214 within the shell member 212.

In order to assure the attainment of the desired orientation of the bearing member 214 within the shell member 212, prior to securement by virtue of the rib 264 entering the annular recess 262, depending fingers 230 will preclude complete insertion of the bearing member 214 into the shell member 212 by abutting the upper lateral surface 254 of flange 246 when the bearing member 214 is in the longitudinal position shown in FIG. 19 and the bearing member 214 is not in the desired orientation. Upon rotation of the bearing member 214 into the desired orientation, notches 266 in the flange 246 are registered with corresponding fingers 230. The notches 266 are configured for allowing the fingers 230 to enter the notches 266, thereby permitting full engagement of the bearing member 214 within the shell member 212 upon proper orientation of the bearing member 214 relative to the shell member 212. Upon such full engagement of the bearing member 214 within the shell member 212, sharp edges 267 on the fingers 230 are embedded within the material of bearing member 214, as shown at 268, for precluding micromotions between the bearing member 214 and the shell member 212. A small clearance at 269, between portions of the upper lateral surface 254 and corresponding confronting portions of the lower end 224 of the shell member 212, provide purchases for any desired subsequent removal of the bearing member 214 from the shell member 212.

Figure 21:
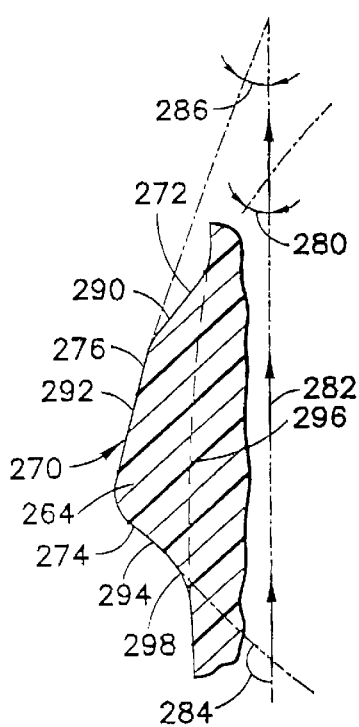
FIG. 21 is an enlarged fragmentary view of a portion of FIG. 18.

Turning now to FIG. 21, rib 264 is provided with a cross-sectional profile contour configuration 270 for facilitating engagement of the rib 264 within the recess 262, while effecting an enhanced connection between the bearing member 214 and the shell member 212. Profile contour configuration 270 includes an upper section 272 confronting the top 244 at the upper end of the bearing member 214, a lower section 274 confronting the base 242 at the lower end of the bearing member 214, and an intermediate section 276 extending between the upper and lower sections 272 and 274. The upper section 272 makes an acute angle 280 with axial direction 282, and the lower section 274 makes an obtuse angle 284 with the axial direction 282. The intermediate section 276 makes an acute angle 286 with the axial direction 282, the acute angle 286 being smaller than the acute angle 260 so as to establish tapered surfaces 290 and 292 along the upper and intermediate sections 272 and 276, respectively, while the obtuse angle 284 establishes a locking surface 294 along the lower section 274. The tapered surfaces 290 and 292 facilitate the engagement of rib 264 within recess 262 during assembly and the locking surface 294 retains the rib 264 within the recess 262 once assembly is complete. The overall profile contour configuration 270 maximizes the area 296 at the root 298 of the rib 264 so that the resistance to shear of the material of the bearing member 214 at the root 298 of the rib 264 is maximized. At the same time, a sharp edge 300 which extends along the recess 262, engages the rib 264 at the locking surface 294, as illustrated at 302, to preclude micromotions between the bearing member 214 and the shell member 212.

Again, should the surgeon determine, either on the basis of a pre-operative assessment of a patient or during the course of the implant procedure, that based upon the needs of a particular patient, as determined by the pre-operative assessment or by an evaluation of conditions encountered at the particular implant site, a bearing material having characteristics other than those of the material of bearing member 214 would be more appropriate, acetabular cup assembly 200 provides the surgeon with the ability to choose, from a kit of component parts providing a plurality of bearing members, a bearing member having a bearing material which exhibits characteristics more appropriate to the needs of that particular patient. Thus, as seen in FIGS. 22 through 25, an alternate bearing member 310 is constructed of a ceramic material and includes a generally domed exterior portion 312 which extends to a top 314. A bearing socket 316 extends upwardly into the bearing member 310 and provides a spherical bearing surface 318 for a complementary femoral head 320 of the proximal end 322 of a femoral component 324.

As in the embodiment described above in connection with FIGS. 7 through 10, bearing member 310 is provided with an external receptor element in the form of a generally cylindrical securement surface 330 which extends essentially parallel to central axis C of the bearing member 310, between lower end 332 of the bearing member 310 and the domed exterior portion 312. In order to enable simplified interoperative securement of the bearing member 310 within shell member 212, subsequent to locating and seating shell member 212 within the acetabulum, securing mechanism 260 provides appropriate mating tapered surfaces. Thus, securing mechanism 260 includes a metallic securing member shown in the form of a sleeve 340 having an annular ring portion 342 adjacent a lower end 344 and a domed portion 346 extending between the ring portion 342 and an upper end 348. The domed portion 346 is to be received within the counterpart portion of the inner cavity 220 of the shell member 212, and the ring portion 342 is provided with an external securing element in the form of an external seating surface 350 and an internal receptor element in the form of a generally cylindrical internal securement surface 352. The configuration of the internal securement surface 352 and the configuration of the external securement surface 330 are compatible with the particular characteristics of the material of the bearing member 310 so that upon engagement of the external securement surface 330 with the internal securement surface 352, as by an interference fit, the bearing member 310 is secured to the sleeve 340.

Figure 24:
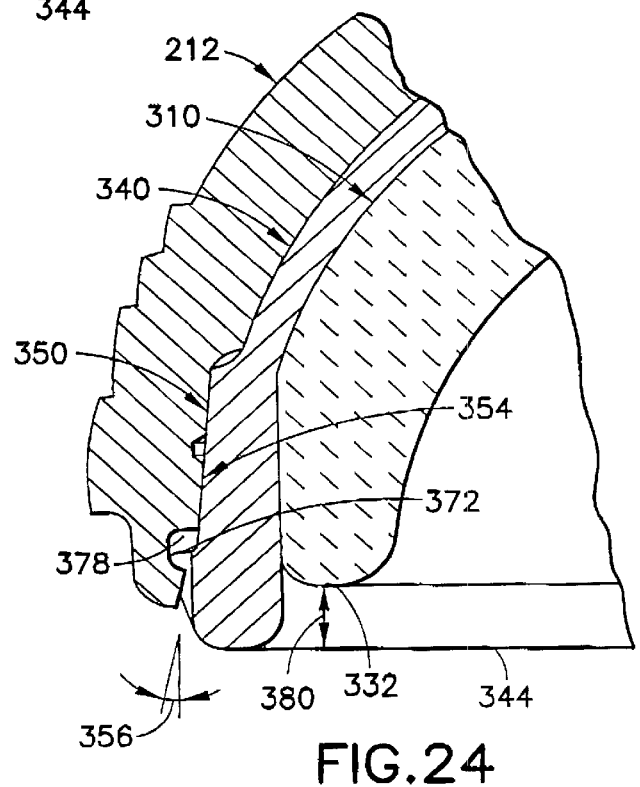
FIG. 24 is an enlarged fragmentary view similar to FIG. 23, and showing the securing component and bearing component assembly assembled within the acetabular shell.

Securing mechanism 260 further includes an internal securing element in the form of internal seating surface 354 located on the shell member 212, within the cavity 220 adjacent the lower end 224 of the shell member 212. Internal seating surface 354 is generally complementary to external seating surface 350 for mating engagement of the seating surfaces 350 and 354, as seen in FIG. 24. The seating surfaces 350 and 354 are provided with a tapered configuration, as illustrated by angle 356, the taper of the configuration being compatible with the securing characteristics of the material of the sleeve 340 and the shell member 212 such that the sleeve 340 is secured within the shell member 212 by virtue of the locking of the tapered seating surfaces 350 and 354 in response to engagement of the seating surfaces 350 and 354. In the preferred embodiment, the shell member 212 and the sleeve 340 are constructed of commercially pure titanium and the angle 356 is about 60. Seating surface 354 includes an upper end 360 and a lower end 362 and is divided by the recess 262 into an upper segment 364 and a lower segment 366. By placing the recess 262 essentially midway between the upper end 360 and the lower end 362, engagement of the seating surfaces 350 and 354, and the locking of the seating surfaces 350 and 354 in response to such engagement is facilitated, by virtue of the locking being accomplished along segments 364 and 366 having generally the same, and therefore maximized, axial length. In this manner, the effectiveness of the seating surface 354 in assuring appropriate alignment between the sleeve 340 and the shell 212 as the sleeve 340 is inserted into the shell 212 and in subsequently attaining the desired locking engagement with seating surface 350 is not compromised by the presence of the recess 262.

A flange 370 extends laterally outwardly from the lower end 344 of the sleeve 340. In order to assure the attainment of the desired orientation of the sleeve 340, and the bearing member 310, within the shell member 212, prior to securement by virtue of the full seating of the sleeve 340 and bearing member 310, depending fingers 230 will preclude complete insertion of the sleeve 340 into the shell member 212 by abutting upper lateral surface 372 of flange 370 when the sleeve 340 is in the longitudinal position shown in FIG. 23 and the sleeve 340 is not in the desired orientation. Upon rotation of the sleeve 340 into the desired orientation, notches 376 in the flange 370 are registered with corresponding fingers 230. The notches 376 are configured for allowing the fingers 230 to enter the notches 376, thereby permitting full engagement of the sleeve 340, and bearing member 310, within the shell member 212 upon proper orientation and axial alignment of the sleeve 340 relative to the shell member 212. A small clearance at 378, between portions of the upper lateral surface 372 and corresponding confronting portions of the lower end 224 of the shell member 212, provide purchases for any desired subsequent removal of the bearing member 310 from the shell member 212.

Figure 23:
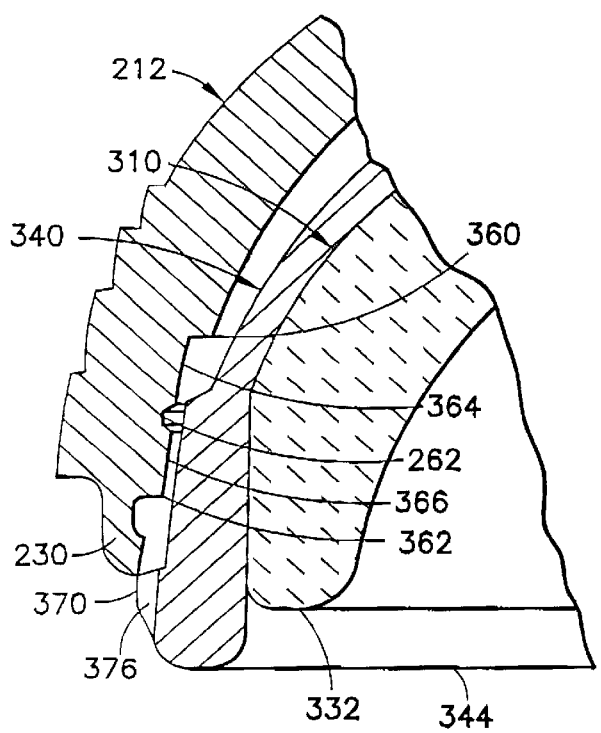
FIG. 23 is an enlarged fragmentary view of the portion of the securing component and bearing component assembly as the assembly is being inserted into the acetabular shell.
Figure 25:
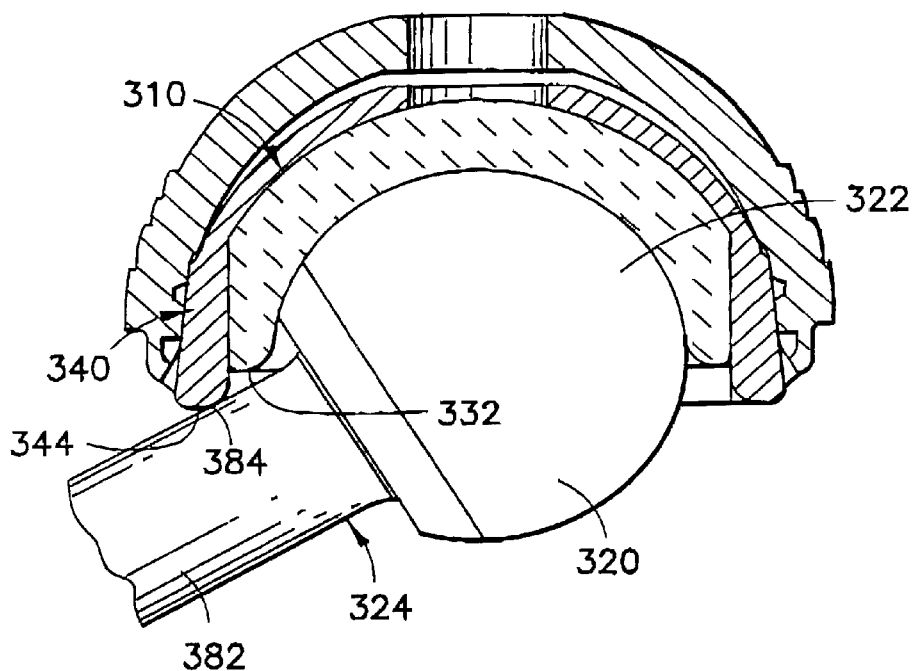
FIG. 25 is a longitudinal cross-sectional view of the assembled securing component, bearing component and acetabular shell, with a femoral head of a femoral component engaged with the securing component.

As best seen in FIG. 25, as well as in FIGS. 23 and 24, the lower end 332 of the bearing member 310 is spaced upwardly from the lower end 344 of the sleeve 340 a prescribed distance 380. With the femoral head 320 of the femoral component 324 engaged in the bearing surface 318 of the bearing member 310, rotational movement of the proximal end 322 of the femoral component 324 is limited by engagement of neck 382 of the femoral component 324 with the lower end 344 of the sleeve 340, as illustrated at 384. In this manner, impingement of the proximal end 322 of the femoral component 324 upon the bearing member 310 is precluded, thus eliminating a potential source of damage to the bearing member 310 when the acetabular cup assembly 200 is in service.

Figure 26:
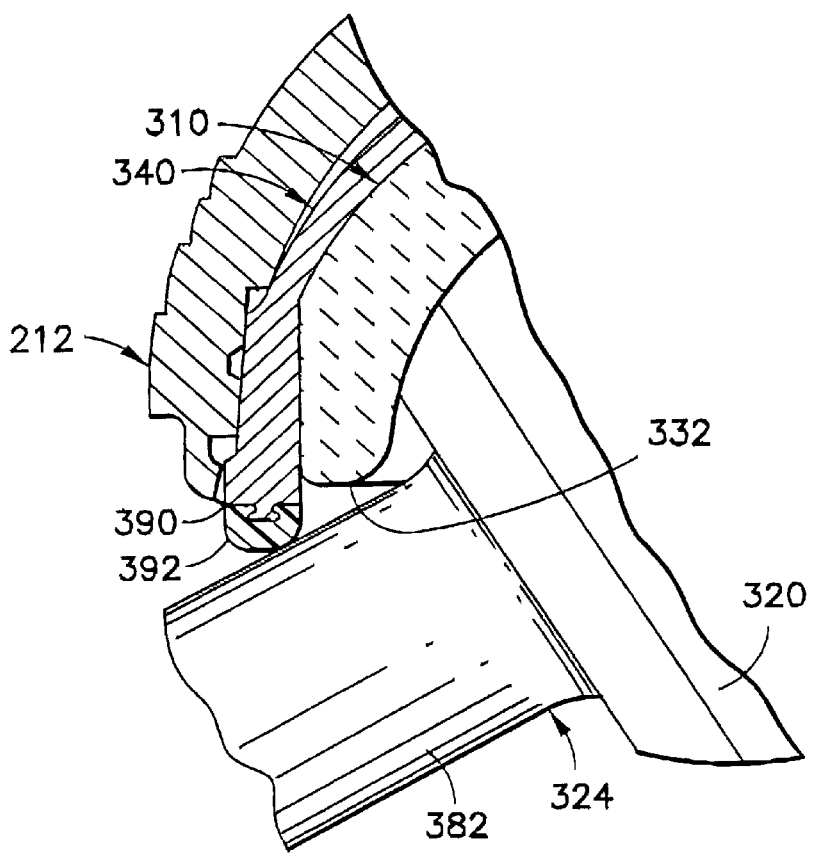
FIG. 26 is an enlarged fragmentary longitudinal cross-sectional view of a modified construction.

In the modification illustrated in FIG. 26, the lower end of the sleeve 340 is modified, as shown at 390, to receive a ring-like cushion 392 affixed to the lower end 390, the cushion 392 being constructed of a resilient synthetic polymeric material, the cushion 392 thus being interposed between the lower end of the sleeve 340 and the proximal end 322 of the femoral component 324 so as essentially to absorb shock connected with engagement of the proximal end 322 of the femoral component 324 with the sleeve 340.

It will be seen that acetabular cup assemblies 20 and 200 provide a surgeon with a wide range of choices for a pre-operative or an interoperative selection of characteristics of the bearing member of the acetabular cup assembly, with simplicity and lowered cost. Such characteristics include material, size, positioning and orientation. As such, the present invention attains the several objects and advantages summarized above, namely: Accommodates a wide choice of bearing materials in the bearing member of an acetabular cup assembly, while utilizing a common acetabular shell; enables the choice of size, position and orientation of the bearing surface of a bearing member selected for assembly with a particular acetabular shell; increases the range of bearing materials, as well as bearing size, positioning and orientation, and renders the choices available in a practical manner for either pre-operative or interoperative selection; allows a surgeon greater latitude in accommodating the needs of different patients while meeting the requirements imposed by various conditions encountered at a particular implant site, and enables appropriate choices to be made interoperatively, as well as pre-operatively; promotes greater accuracy in the replacement of a natural hip joint, with increased economy; provides a surgeon with the ability to make both pre-operative choices and interoperative choices from a wider range of options; enables the securement of a bearing member of selected material within a common acetabular shell, with increased ease and economy, and without complex, specialized instruments; provides an acetabular cup assembly having a bearing member of appropriate bearing material and accurate sizing, positioning and orientation, with economy of manufacture and use, and long-term reliability.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An acetabular cup assembly for receiving a proximal end of a femoral component of a prosthetic hip implant, the femoral component including a head member and a neck member depending from the head member in a distal direction, the acetabular cup assembly having an external shell member with an internal cavity, and an internal bearing member for securement within the cavity to receive the head member of the femoral component for rotational movement within the bearing member, the internal bearing member being selected from a plurality of bearing members having different characteristics, including different securement characteristics, such that the acetabular cup assembly selectively is provided with characteristics corresponding to the characteristics of the selected internal bearing member, the acetabular cup assembly comprising:

a metallic securing member for reception within the cavity of the shell member, the securing member extending between an upper end and a lower end and including an external securing element and an internal receptor element;

an external receptor element on the bearing member, the external receptor element and the internal receptor element having interengagable structures compatible with the securement characteristics of the selected bearing member such that upon engagement of the external receptor element with the internal receptor element the internal bearing member is secured to the securing member with the lower end of the bearing member spaced upwardly a prescribed distance from the lower end of the securing member; and an internal securing element within the cavity of the shell member, the internal securing element being essentially complementary to the external securing element of the securing member such that upon selective engagement of the external securing element with the internal securing element the securing member is secured selectively within the shell member;

the prescribed distance between the lower end of the bearing member and the lower end of the securing member being such that contact between the neck member of the femoral component and the lower end of the securing member precludes deleterious impingement of any portion of the femoral component distal of the head member upon the bearing member.

2. The invention of claim 1 wherein the internal securing element of the shell member and the external securing element of the securing member include complementary tapered securing surfaces for interlocking in response to seating engagement of the complementary securing surfaces.

3. The invention of claim 2 wherein the internal receptor element of the securing member and the external receptor element of the bearing member include complementary securing surfaces for interlocking upon seating engagement of the complementary securing surfaces.

4. The invention of claim 3 wherein the complementary securing surfaces of the external receptor element include complementary tapered surfaces for interlocking in response to seating engagement of the complementary tapered surfaces.

5. The invention of claim 4 wherein the shell member includes a lower end and an upper end, the cavity extends from the lower end toward the upper end of the shell member, and the internal securing element is located adjacent the lower end of the shell member.

6. The invention of claim 5 wherein the external securing element is located adjacent the lower end of the metallic securing. member.

7. The invention of claim 6 wherein the metallic securing member includes a ring portion adjacent the lower end and a domed portion extending between the ring portion and the upper end of the metallic securing member.

8. The invention of claim 7 wherein the shell member includes at least one depending finger extending downwardly from the lower end of the shell member, and the metallic securing member includes a flange extending laterally outwardly from the lower end of the securing member for engaging the depending finger to preclude the seating engagement of the complementary tapered securing surfaces of the shell member and the securing member, and at least one notch in the flange, the notch being configured for accepting entrance of the finger into the notch upon alignment of the notch with the finger, such alignment of the notch with the finger being accomplished upon a desired orientation and alignment of the securing member, and the bearing member therein, relative to the shell member, for enabling seating engagement of the complementary tapered surfaces with the bearing member in the desired orientation and alignment.

9. The invention of claim 1 wherein the shell member includes a lower end and an upper end, the cavity extends from the lower end toward the upper end of the shell member, the internal receptor element includes a central axis extending longitudinally between the lower end and the upper end of the shell member, the external securing element includes a central axis extending longitudinally between the lower end and the upper end of the shell member, and the central axis of the internal receptor element is offset laterally from the central axis of the external securing element.

10. The invention of claim 9 wherein the internal securing element of the shell member and the external securing element of the securing member include complementary tapered securing surfaces for interlocking in response to seating engagement of the complementary securing surfaces.

11. The invention of claim 10 wherein the internal receptor element of the securing member and the external receptor element of the bearing member include complementary securing surfaces for interlocking upon seating engagement of the complementary securing surfaces.

12. The invention of claim 11 wherein the complementary securing surfaces of the external receptor element include complementary tapered surfaces for interlocking in response to seating engagement of the complementary tapered surfaces.

13. The invention of claim 12 wherein the shell member includes at least one depending finger extending downwardly from the lower end of the shell member, and the metallic securing member includes a flange extending laterally outwardly from the lower end of the securing member for engaging the depending finger to preclude the seating engagement of the complementary tapered securing surfaces of the shell member and the securing member, and at least one notch in the flange, the notch being configured for accepting entrance of the finger into the notch upon alignment of the notch with the finger, such alignment of the notch with the finger being accomplished upon a desired orientation and alignment of the securing member, and the bearing member therein, relative to the shell member, for enabling seating engagement of the complementary tapered surfaces with the bearing member in the desired orientation and alignment.

14. The invention of claim 1 wherein the shell member includes a lower end and an upper end, the cavity extends from the lower end toward the upper end of the shell member, the internal receptor element includes a central axis extending longitudinally between the lower end and the upper end of the shell member, the external securing element includes a central axis extending longitudinally between the lower end and the upper end of the shell member, and the central axis of the internal receptor element makes an acute angle with the central axis of the external securing element.

15. The invention of claim 14 wherein the internal securing element of the shell member and the external securing element of the securing member include complementary tapered securing surfaces for interlocking in response to seating engagement of the complementary securing surfaces.

16. The invention of claim 15 wherein the internal receptor element of the securing member and the external receptor element of the bearing member include complementary securing surfaces for interlocking upon seating engagement of the complementary securing surfaces.

17. The invention of claim 16 wherein the complementary securing surfaces of the external receptor element include complementary tapered surfaces for interlocking in response to seating engagement of the complementary tapered surfaces.

18. The invention of claim 17 wherein the shell member includes at least one depending finger extending downwardly from the lower end of the shell member, and the metallic securing member includes a flange extending laterally outwardly from the lower end of the securing member for engaging the depending finger to preclude the seating engagement of the complementary tapered securing surfaces of the shell member and the securing member, and at least one notch in the flange, the notch being configured for accepting entrance of the finger into the notch upon alignment of the notch with the finger, such alignment of the notch with the finger being accomplished upon a desired orientation and alignment of the securing member, and the bearing member therein, relative to the shell member, for enabling seating engagement of the complementary tapered surfaces with the bearing member in the desired orientation and alignment.

19. The invention of claim 1 including a cushion at the lower end of the securing member for interposition between the securing member and the femoral component.

20. A shell member for use in an acetabular cup assembly having an internal bearing member for selective securement within the shell member interoperatively, the internal bearing member being selected from a plurality of bearing members having different characteristics, including different securement characteristics, such that the acetabular cup assembly selectively is provided with characteristics corresponding to the characteristics of the selected internal bearing member, the shell member comprising:

an internal cavity;
a first securing element within the cavity of the shell member, the first securing element having a first securing structure compatible with the securement characteristics of at least one of the plurality of internal bearing members; and
a second securing element within the cavity of the shell member, the second securing element having a second securing structure compatible with the securement characteristics of at least another of the plurality of internal bearing members;
the first and second securing structures being juxtaposed with one another and placed at relative locations such that the effectiveness of each of the first and second securing elements is maintained while in the presence of the other of the first and second securing elements, whereby the one and the another of the internal bearing members each is selectable for effective selective securement within the shell member to complete the acetabular cup assembly interoperatively.

21. The invention of claim 20 wherein the shell member includes a lower end and an upper end, the cavity extends from the lower end toward the upper end of the shell member, and the first and second securing elements are located adjacent the lower end of the shell member.

22. The invention of claim 21 wherein the bearing member includes a rib projecting from the bearing member, and the first securing element includes a recess in the shell member for receiving the rib of the bearing member.

23. The invention of claim 21 wherein the bearing member includes an external securing surface, and the second securing element includes an internal securing surface, the external securing surface and the internal securing surface having complementary tapered configurations for interlocking in response to seating engagement of the complementary tapered configurations.

24. The invention of claim 23 wherein the bearing member includes a rib projecting from the bearing member, and the first securing element includes a recess in the shell member for receiving the rib of the bearing member, the tapered configuration of the internal securing surface extends between an upper end and a lower end, and the recess is located intermediate the upper end and the lower end of the tapered configuration of the internal securing surface to establish an upper internal securing surface segment and a lower internal securing surface segment, with each of the upper and lower internal securing surface segments having a length between the upper and lower ends of the internal securing surface sufficient to maintain securing effectiveness throughout the internal securing surface.

25. The invention of claim 24 wherein the recess is located essentially midway between the upper and lower ends of the internal securing surface.

26. The invention of claim 25 wherein the bearing member includes an upper end and a lower end spaced in an axial direction from the upper end, and the rib includes a cross-sectional profile contour configuration having an upper section confronting the upper end of the bearing member, a lower section confronting the lower end of the bearing member, and an intermediate section between the upper and lower sections, the upper section making a first acute angle with the axial direction, the lower section making an obtuse angle with the axial direction, and the intermediate section making a second acute angle with the axial direction, the second acute angle being smaller than the first acute angle so as to establish tapered surfaces along the upper and intermediate sections for facilitating engagement of the rib within the recess, and a locking surface along the lower section for retaining the rib within the recess, while providing the rib with resistance to shearing from the bearing member.

27. A kit of component parts for assembling an acetabular cup assembly having an internal bearing member for selective securement within a shell member interoperatively, the kit comprising:

a plurality of bearing members having different characteristics, including different securement characteristics, such that the acetabular cup assembly selectively is provided with characteristics corresponding to the characteristics of a selected one of the internal bearing members;
the shell member comprising:
an internal cavity;
a first securing element within the cavity of the shell member, the first securing element having a first securing structure compatible with the securement characteristics of at least one of the plurality of internal bearing members; and
a second securing element within the cavity of the shell member, the second securing element having a second securing structure compatible with the securement characteristics of at least another of the plurality of internal bearing members; the first and second securing elements being juxtaposed with one another and placed at relative locations such that the effectiveness of each of the first and second securing elements is maintained while in the presence of the other of the first and second securing elements, whereby the one and the another of the internal bearing members each is selectable for effective selective securement within the shell member as the selected one bearing member to complete the acetabular cup assembly interoperatively.

28. The invention of claim 27 wherein the shell member includes a lower end and an upper end, the cavity extends from the lower end toward the upper end of the shell member, and the first and second securing elements are located adjacent the lower end of the shell member.

29. The invention of claim 28 wherein the bearing member includes a rib projecting from the bearing member, and the first securing element includes a recess in the shell member for receiving the rib of the bearing member.

30. The invention of claim 28 wherein the bearing member includes an external securing surface, and the second securing element includes an internal securing surface, the external securing surface and the internal securing surface having complementary tapered configurations for interlocking in response to seating engagement of the complementary tapered configurations.

31. The invention of claim 30 wherein the bearing member includes a rib projecting from the bearing member, and the first securing element includes a recess in the shell member for receiving the rib of the bearing member, the tapered configuration of the internal securing surface extends between an upper end and a lower end, and the recess is located intermediate the upper end and the lower end of the tapered configuration of the internal securing surface to establish an upper internal securing surface segment and a lower internal securing surface segment, with each of the upper and lower internal securing surface segments having a length between the upper and lower ends of the internal securing surface sufficient to maintain securing effectiveness throughout the internal securing surface.

32. The invention of claim 31 wherein the recess is located essentially midway between the upper and lower ends of the internal securing surface.

33. An improvement in a method for implanting an acetabular cup assembly having an external shell member with an internal cavity, and an internal bearing member for securement within the cavity interoperatively, the internal bearing member being selected from a plurality of bearing members having different characteristics, including different securement characteristics, such that the acetabular cup assembly selectively is provided with characteristics corresponding to the characteristics of the selected internal bearing member, the improvement comprising the steps of:

providing a first securing element within the cavity of the shell member, the first securing element having a first securing structure compatible with the securement characteristics of at least one of the plurality of internal bearing members;

providing a second securing element within the cavity of the shell member, the second securing element having a second securing structure compatible with the securement characteristics of at least another of the plurality of internal bearing members; and selecting the one or the another of the internal bearing members and securing the selected internal bearing member within the shell member by engaging the selected internal bearing member with the corresponding first securing element or second securing element for completion of the acetabular cup assembly interoperatively.

34. The method of claim 33 including implanting the shell member at an implant site prior to securing the selected internal bearing member within the cavity of the shell member.

* * * * *

(12) EX PARTE REEXAMINATION CERTIFICATE (7911th)
United States Patent
Sheldon et al.

(10) Number: US 6,475,243 C1
(45) Certificate Issued: Dec. 7, 2010

(54) ACETABULAR CUP ASSEMBLY WITH SELECTED BEARING

(75) Inventors: Michael B. Sheldon, Pymble (AU); Nicholas N. G. Dong, Little Falls, NJ (US)

(73) Assignee: Howmedica Osteonics Corp., Allendale, NJ (US)

Reexamination Request:
No. 90/009,406, Feb. 10, 2009

Reexamination Certificate for:
Patent No.: 6,475,243
Issued: Nov. 5, 2002
Appl. No.: 09/665,025
Filed: Sep. 19, 2000

Related U.S. Application Data

(63) Continuation-in-part of application No. 09/083,406, filed on May 22, 1998, now abandoned.

(51) Int. Cl.
    *A61F 2/32* (2006.01)

(52) U.S. Cl. .................. 623/22.28; 623/22.21
(58) Field of Classification Search .......... None
    See application file for complete search history.

(56) References Cited

U.S. PATENT DOCUMENTS

| | | | |
|---|---|---|---|
| 3,894,297 A | 7/1975 | Mittelmeier et al. | |
| 4,241,463 A | 12/1980 | Khovaylo | 623/22.2 |
| 4,650,491 A | 3/1987 | Parchinski | 623/22.28 |
| 5,310,408 A | 5/1994 | Schryver et al. | 623/22.37 |
| 5,725,591 A | 3/1998 | DeCarlo, Jr. et al. | |
| 5,919,236 A * | 7/1999 | Pfaff et al. | 623/18.11 |
| 6,589,284 B1 | 7/2003 | Silberer | 623/22.29 |

FOREIGN PATENT DOCUMENTS

| | | |
|---|---|---|
| DE | 8500869 | 12/1985 |
| DE | 4222218 | 1/1994 |
| DE | 4335931 | 4/1995 |
| DE | 29517637 | 10/1996 |
| DE | 19616058 | 10/1997 |
| DE | 19620750 | 1/1998 |
| DE | 19701536 | 2/1998 |
| DE | 19654409 | 4/1998 |
| EP | 0091315 | 10/1983 |
| EP | 694294 | 1/1996 |
| FR | 2682588 | 4/1993 |

OTHER PUBLICATIONS

Transcend Articulation System, Ceramic on ceramic articulation. Wright Medical Technology, Inc., 1997.
Contact SPH Cups System, non–cemented. Lima–Lto Medial Systems, undated.
Orthop. J. China, 6:711–715, 1999.
Proc.5th CeramTec Symposium, p. 39–45, Feb. 18–19, 2000.
Protek: SulzerMedica, MetaSUL Brochure.

* cited by examiner

*Primary Examiner*—Glenn K. Dawson

(57) ABSTRACT

An acetabular cup assembly allows pre-operative or interoperative selection and securement of a bearing member within a shell member of the acetabular cup assembly, the bearing member being selected from a plurality of bearing members having different characteristics, including bearing characteristics, securement characteristics, position characteristics and orientation characteristics, so as to enable a surgeon to select those characteristics most appropriate to a particular patient, as determined by a pre-operative assessment or by an evaluation of conditions encountered at an implant site during the implant procedure, and to incorporate the desired characteristics into the acetabular cup assembly with ease and economy.

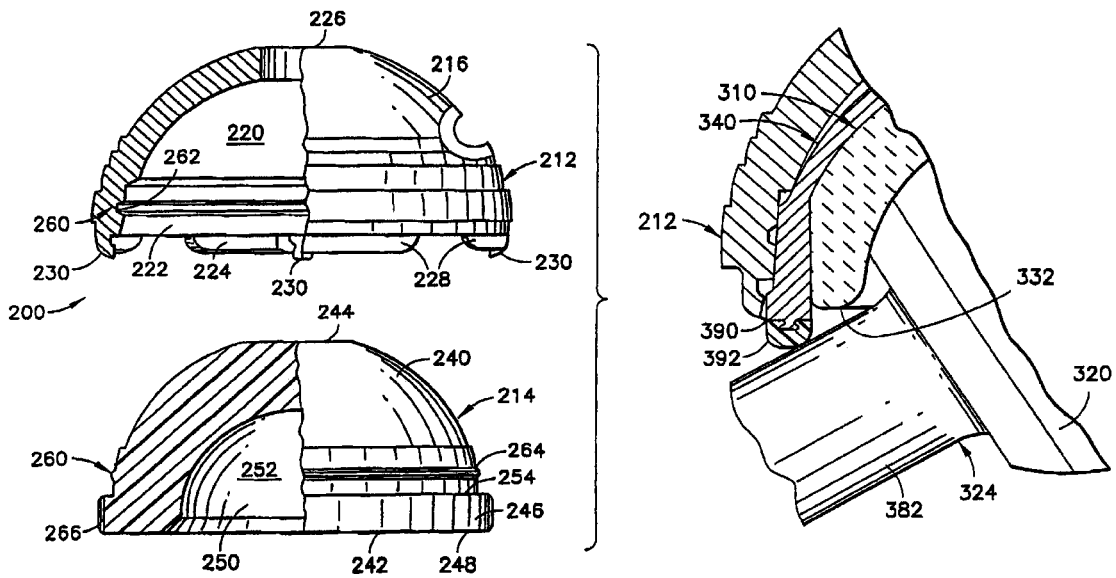

US 6,475,243 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 21-24, 26, 33 and 34 are cancelled.

Claims 20 and 25 are determined to be patentable as amended.

New claims 35-55 are added and determined to be patentable.

Claims 1-19 and 27-32 were not reexamined.

20. [A] *An assembly having a* shell member [for use in an acetabular cup assembly having] *and* an internal bearing member for selective securement within the shell member interoperatively, the internal bearing member being selected from a plurality of bearing members having different characteristics, including different securement characteristics, such that the acetabular cup assembly selectively is provided with characteristics corresponding to the characteristics of the selected internal bearing member, the shell member comprising:
   an internal cavity;
   a first securing element within the cavity of the shell member, the first securing element having a first securing structure compatible with the securement characteristics of at least one of the plurality of internal bearing members; and
   a second securing element within the cavity of the shell member, the second securing element having a second securing structure compatible with the securement characteristics of at least another of the plurality of internal bearing members;
   the first and second securing structures being juxtaposed with one another and placed at relative locations such that the effectiveness of each of the first and second securing elements is maintained while in the presence of the other of the first and second securing elements, whereby the one and the another of the internal bearing members each is selectable for effective selective securement within the shell member to complete the acetabular cup assembly interoperatively;
   *wherein the shell member includes a lower end and an upper end, the cavity extends from the lower end toward the upper end of the shell member, and the first and second securing elements are located adjacent the lower end of the shell member;*
   *wherein the bearing member includes an external securing surface, and the second securing element includes an internal securing surface, the external securing surface and the internal securing surface having complementary tapered configurations for interlocking in response to seating engagement of the complementary tapered configurations; and*
   *wherein the bearing member includes a rib projecting from the bearing member, and the first securing element includes a recess in the shell member for receiving the rib of the bearing member, the tapered configuration of the internal securing surface extends between an upper end and a lower end.*

25. The invention of claim [24] *20* wherein the recess is located essentially midway between the upper and lower ends of the internal securing surface.

*35. The assembly of claim 20, further comprising at least one anti-rotation element configured to engage a complementary anti-rotation element of the bearing member.*

*36. The assembly of claim 20, wherein the different characteristics of the internal bearing members include different materials.*

*37. The assembly of claim 36, wherein the material of the at least one of the plurality of internal bearing members includes at least one of ceramic, metal, and plastic.*

*38. The assembly of claim 37, wherein the at least one of the plurality of internal bearing members comprises a projection extending from the bearing member, and the first securing element includes a recess in the shell member for receiving the projection of the bearing member.*

*39. The assembly of claim 20, wherein the bearing member includes a lower end and an upper end, and the lower end of the bearing member extends beyond the lower end of the shell member when the bearing member is assembled in the shell member.*

*40. The assembly of claim 20, wherein the recess is located intermediate the upper end and the lower end of the tapered configuration of the internal securing surface to establish an upper internal securing surface segment and a lower internal securing surface segment, with each of the upper and lower internal securing surface segments having a length between the upper and lower ends of the internal securing surface sufficient to maintain securing effectiveness throughout the internal securing surface.*

*41. An acetabular cup system, comprising:*
   *a plurality of internal bearing members, each comprising:*
      *an inner bearing surface for receiving a head member;*
      *an outer surface; and*
      *a central bearing member axis defined by the outer surface;*
   *the internal bearing members having different characteristics, including different axial securement characteristics and different material characteristics, wherein (i) at least one first internal bearing member of the plurality comprises a polyethylene bearing surface and a securement projection on the outer surface, and (ii) at least one second internal bearing member of the plurality comprises a metal or ceramic bearing surface and an outer securement taper extending axially; and*
   *a shell member, comprising:*
      *an external surface, an internal surface, a central shell axis which coincides with the central bearing member axis when assembled, the external surface having an apex at one end and a peripheral end surface at the opposite end which is the outermost axial extent of the shell member at that opposite end, the internal surface defining an internal cavity;*
      *at least one securement recess in the internal surface within the cavity of the shell member and spaced axially from the peripheral end surface and not extending to the external surface, the securement recess being compatible with the securement projection of the at least one first internal bearing member of the plurality of internal bearing members to axi-* ally secure the first internal bearing member within the shell member; and an internal securement taper on the internal surface within the cavity of the shell member, the internal securement taper extending axially and being compatible with the outer securement taper of the at least one second internal bearing member of the plurality of internal bearing members to axially secure the second internal bearing member within the shell member;

the securement recess and the internal securement taper being juxtaposed with one another and placed at relative locations such that the effectiveness of each of the securement recess and the internal securement taper is maintained while in the presence of the other of the securement recess and the internal securement taper, whereby the first and the second of the internal bearing members each is selectable for effective selective axial securement within the cavity of the shell member to complete the acetabular cup assembly intraoperatively.

42. The system of claim 41, wherein the different characteristics of the plurality of bearing members include different orientations of a bearing socket relative to the cavity of the shell member when the bearing member and the shell member are in seated engagement.

43. The system of claim 41, wherein the different characteristics of the plurality of bearing members include different locations of a bearing socket relative to the cavity of the shell member when the bearing member and the shell member are in seated engagement.

44. The system of claim 41, wherein the securement recess and the securement taper are located adjacent the peripheral end surface of the shell member.

45. The system of claim 41, the bearing member further including at least one bearing anti-rotation element and the shell member further including at least one shell anti-rotation element compatible with the bearing anti-rotation element to rotationally fix the bearing member within the cavity of the shell member.

46. The system of claim 45, wherein the bearing anti-rotation element is on the outer surface of the bearing member and the shell anti-rotation element is a recess that extends into the peripheral end surface of the shell member.

47. The system of claim 41, wherein the bearing member extends beyond the peripheral end surface of the shell member when the bearing member is assembled in the shell member.

48. The system of claim 41, wherein the recess extends circumferentially about the cavity of the shell member.

49. An acetabular cup assembly, comprising:

a first internal bearing member, comprising:
  an inner surface for receiving a head member;
  an outer surface;

wherein the internal bearing is selected from a plurality of bearing members having different characteristics, including different securement characteristics and different material characteristics, such that the acetabular cup assembly is provided with characteristics corresponding to the characteristics of the selected internal bearing member; and a shell member, comprising:
  an internal cavity;
  a first securing element within the cavity of the shell member, the first securing element having a first securing structure compatible with the securement characteristics of at least one of the plurality of internal bearing members; and a second securing element within the cavity of the shell member, the second securing element having a second securing structure compatible with the securement characteristics of at least another of the plurality of internal bearing members;

the first and second securing structures being juxtaposed with one another and placed at relative locations such that the effectiveness of each of the first and second securing elements is maintained while in the presence of the other of the first and second securing elements, whereby the one and the another of the internal bearing members each is selectable for effective selective securement within the shell member to complete the acetabular cup assembly interoperatively;

wherein the material of the selected bearing member includes at least one of ceramic, metal, and plastic; and wherein the outer surface of the selected bearing member includes a metal material and the inner surface of the selected bearing member includes ceramic.

50. An acetabular cup assembly, comprising:

a first internal bearing member, comprising:
  an inner surface for receiving a head member;
  an outer surface;

wherein the internal bearing is selected from a plurality of bearing members having different characteristics, including different securement characteristics and different material characteristics, such that the acetabular cup assembly is provided with characteristics corresponding to the characteristics of the selected internal bearing member; and a shell member, comprising:
  an internal cavity;
  a first securing element within the cavity of the shell member, the first securing element having a first securing structure compatible with the securement characteristics of at least one of the plurality of internal bearing members; and a second securing element within the cavity of the shell member, the second securing element having a second securing structure compatible with the securement characteristics of at least another of the plurality of internal bearing members;

the first and second securing structures being juxtaposed with one another and placed at relative locations such that the effectiveness of each of the first and second securing elements is maintained while in the presence of the other of the first and second securing elements, whereby the one and the another of the internal bearing members each is selectable for effective selective securement within the shell member to complete the acetabular cup assembly interoperatively;

wherein the material of the selected bearing member includes at least one of ceramic, metal, and plastic; and wherein the selected bearing member includes a ceramic bearing surface and a metal securing sleeve, wherein the securing sleeve includes a securement characteristic which is compatible with the first or second securing element of the shell member.

51. An assembly having a shell member and an internal bearing member for selective securement within the shell member interoperatively, the internal bearing member being selected from a plurality of bearing members having different characteristics, including different securement characteristics, such that the acetabular cup assembly selectively is provided with characteristics corresponding to the characteristics of the selected internal bearing member, the shell member comprising:

an internal cavity;
a first securing element within the cavity of the shell member, the first securing element having a first securing structure compatible with the securement characteristics of at least one of the plurality of internal bearing members; and
a second securing element within the cavity of the shell member, the second securing element having a second securing structure compatible with the securement characteristics of at least another of the plurality of internal bearing members;
the first and second securing structures being juxtaposed with one another and placed at relative locations such that the effectiveness of each of the first and second securing elements is maintained while in the presence of the other of the first and second securing elements, whereby the one and the another of the internal bearing members each is selectable for effective selective securement within the shell member to complete the acetabular cup assembly interoperatively;
wherein the different characteristics of the internal bearing members include different materials;
wherein the bearing member includes an external securing surface, and the second securing element includes an internal securing surface, the external securing surface and the internal securing surface having complementary tapered configurations for interlocking in response to seating engagement of the complementary tapered configurations; and
wherein the bearing member includes a ceramic bearing surface and a metal securing sleeve, wherein the securing sleeve includes the tapered configuration complementary with the internal securing surface of the shell member.

52. The shell member of claim 51, wherein the first securing element includes a recess in the internal cavity of the shell member and a first bearing member is polyethylene and further includes a projection extending from the outer surface for reception within the recess.

53. A method for implanting an acetabular cup, comprising the steps of:
providing an external shell member with an internal cavity and a central shell axis, the shell member having at least one securement recess within the cavity of the shell member and an internal securement taper within the cavity of the shell member and extending axially, wherein the securement recess and the internal securement taper are in juxtaposition with one another and placed at relative locations such that the effectiveness of each of the securement recess and the internal securement taper is maintained while in the presence of the other of the securement recess and the internal securement taper;
providing an internal bearing member for axial securement within the cavity intraoperatively and having a central bearing axis, the central shell axis coinciding with the central bearing axis when the shell member and bearing member are assembled, the internal bearing member being selected from a plurality of bearing members having different characteristics, including different material characteristics and axial securement characteristics, wherein (i) at least one first internal bearing member of the plurality comprises a polyethylene bearing surface and a securement projection on the outer surface, and (ii) at least one second internal bearing member of the plurality comprises a metal or ceramic bearing surface and an outer securement taper extending axially, wherein the securement recess is compatible with the securement projection of the first internal bearing member of the plurality of internal bearing members to axially secure the first internal bearing member within the shell member, and the internal securement taper is compatible with the outer securement taper of the second internal bearing member of the plurality of internal bearing members to axially secure the second internal bearing member with the shell;
selecting the first internal bearing member or the second internal bearing member; and
securing the selected internal bearing member within the shell member by engaging the selected internal bearing member with the corresponding securement recess or securement taper for axial securement of the selected bearing member within the shell member and completion of the acetabular cup assembly intraoperatively.

54. The method in claim 53, wherein at least one bearing members among the plurality of bearing members further includes at least one bearing anti-rotation element and the shell member further includes at least one shell anti-rotation element configured to engage the bearing anti-rotation element of a bearing member to rotationally fix the bearing member within the cavity of the shell member.

55. The method of claim 54, wherein the at least one bearing anti-rotation element includes a protrusion, and the shell anti-rotation element includes a recess.

* * * * *